United States Patent
Eaton-Evans et al.

(10) Patent No.: US 11,464,564 B2
(45) Date of Patent: Oct. 11, 2022

(54) MICROWAVE ABLATION PROBE

(71) Applicant: NATIONAL UNIVERSITY OF IRELAND, GALWAY, Galway (IE)

(72) Inventors: Jimmy Eaton-Evans, Galway (IE); Giuseppe Ruvio, Galway (IE); Martin O'Halloran, Galway (IE); Jonathan Bouchier-Hayes, Galway (IE); Mark Bruzzi, Galway (IE)

(73) Assignee: NATIONAL UNIVERSITY OF IRELAND, GALWAY, Galway (IE)

( * ) Notice: Subject to any disclaimer, the term of this patent is extended or adjusted under 35 U.S.C. 154(b) by 146 days.

(21) Appl. No.: 16/638,058

(22) PCT Filed: Jun. 29, 2018

(86) PCT No.: PCT/EP2018/067714
§ 371 (c)(1),
(2) Date: Feb. 10, 2020

(87) PCT Pub. No.: WO2019/029906
PCT Pub. Date: Feb. 14, 2019

(65) Prior Publication Data
US 2020/0205894 A1 Jul. 2, 2020

(30) Foreign Application Priority Data
Aug. 9, 2017 (EP) ..................... 17185646

(51) Int. Cl.
*A61B 18/18* (2006.01)
*A61B 18/00* (2006.01)

(52) U.S. Cl.
CPC . *A61B 18/1815* (2013.01); *A61B 2018/00011* (2013.01); *A61B 2018/00577* (2013.01); *A61B 2018/00821* (2013.01)

(58) Field of Classification Search
CPC ...... A61B 18/1815; A61B 2018/00011; A61B 2018/00577; A61B 2018/00821; A61B 2018/00023; A61B 2018/1892
(Continued)

(56) References Cited

U.S. PATENT DOCUMENTS 5,693,082 A 12/1997 Warner et al.
2003/0065317 A1 4/2003 Rudie et al.
(Continued)

FOREIGN PATENT DOCUMENTS

| JP | 2010-274118 A | 12/2010 |
| JP | 2012-139495 A | 7/2012 |
| JP | 2014-180550 A | 9/2014 |

OTHER PUBLICATIONS

International Search Report and Written Opinion dated Sep. 21, 2018, International Application No. PCT/EP2018/067714, 10 pages.
(Continued)

*Primary Examiner* — Khadijeh A Vahdat
(74) *Attorney, Agent, or Firm* — Husch Blackwell LLP

(57) ABSTRACT

A microwave ablation probe (200; 300; 400), comprising: an applicator (202; 302; 402) arranged to apply microwave radiation to heat surrounding tissue; a feeding cable (204; 304; 404) arranged to supply electromagnetic energy to the applicator; a coolant flow path (206) via which coolant is able to flow; and a choke arranged to reduce power reflected from the applicator (202; 302; 402) along the feeding cable (204; 304; 404). The choke comprises a choke member (208; 209; 308; 408) cooled by coolant flowing in the coolant flow path (206). The choke member (208; 209; 308; 408) extends between two points spaced apart in a direction having at least a component parallel to a longitudinal axis of the feeding cable. The choke member (208; 209; 308; 408) comprises one or more turns extending around the longitu-
(Continued)

dinal axis of the feeding cable. The choke member may be a spiral member (208; 308; 408).

20 Claims, 10 Drawing Sheets

(58) Field of Classification Search
USPC .......................................................... 606/33
See application file for complete search history.

(56) References Cited

U.S. PATENT DOCUMENTS

| | | | |
|---|---|---|---|
| 2009/0187180 A1* | 7/2009 | Brannan | A61B 18/18 606/33 |
| 2012/0203100 A1 | 8/2012 | Weiss et al. | |
| 2012/0259326 A1 | 10/2012 | Brannan et al. | |
| 2015/0216596 A1* | 8/2015 | Brannan | A61B 18/1815 606/33 |
| 2016/0058508 A1* | 3/2016 | Brannan | A61B 18/1815 606/33 |
| 2016/0192987 A1* | 7/2016 | Brannan | A61B 34/10 606/33 |
| 2018/0289388 A1* | 10/2018 | Lenker | A61B 18/1492 |

OTHER PUBLICATIONS

Extended European Search Report dated Jan. 26, 2018, European Application No. 17185646.1, 6 pages.
Translation of Office Action issued for Japanese Patent Application No. JP2020-507621 dated May 24, 2022, 17 pages.

* cited by examiner

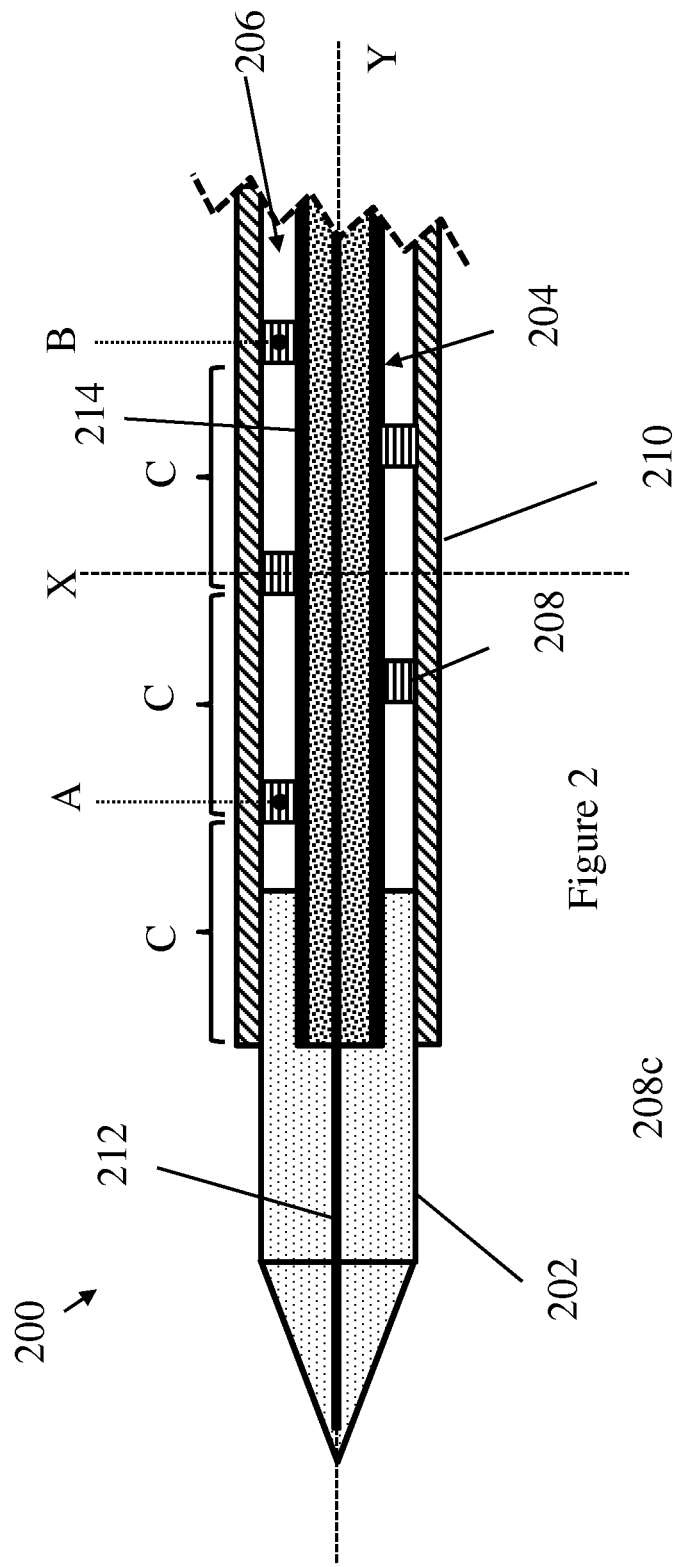
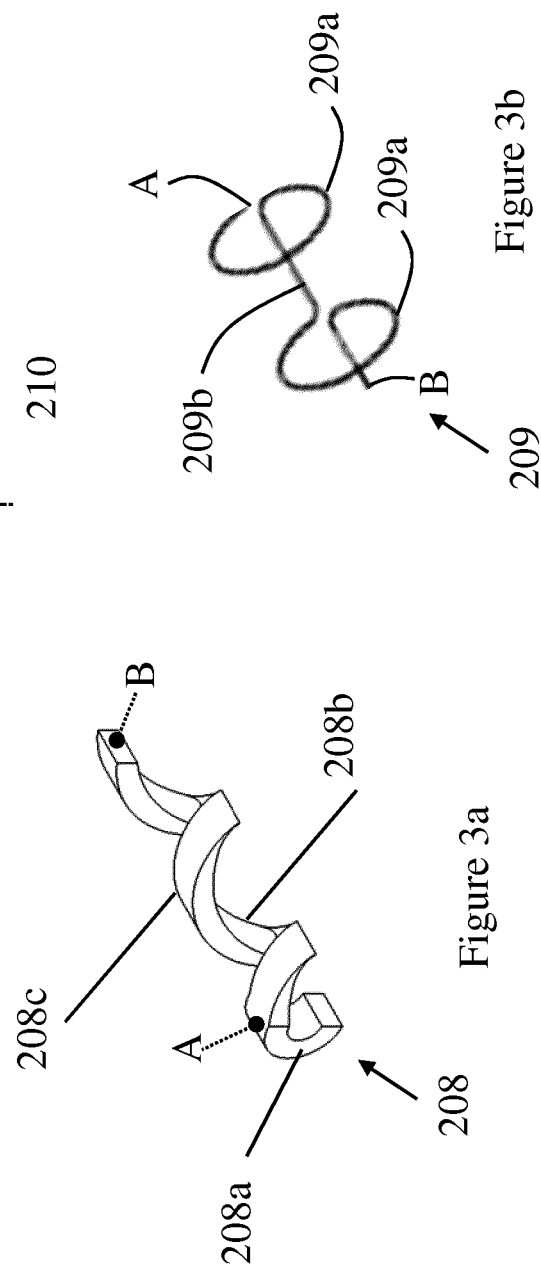
Figure 2
Figure 3a
Figure 3b

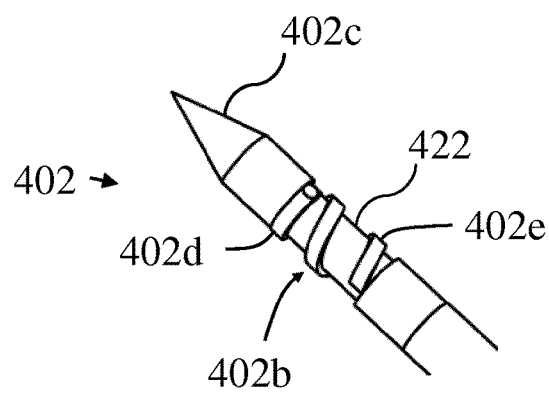
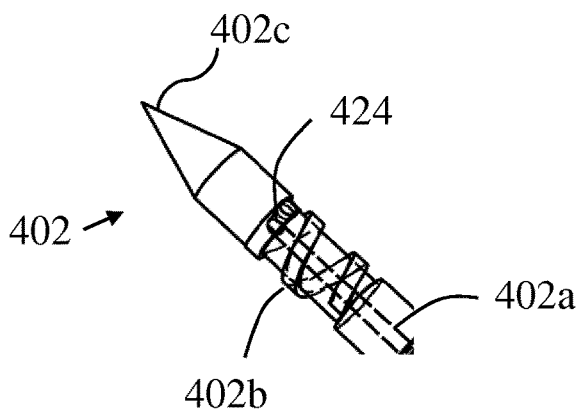
Figure 11a
Figure 11b
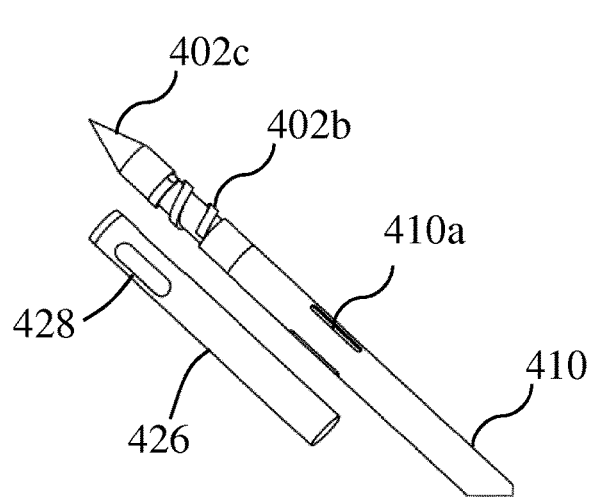
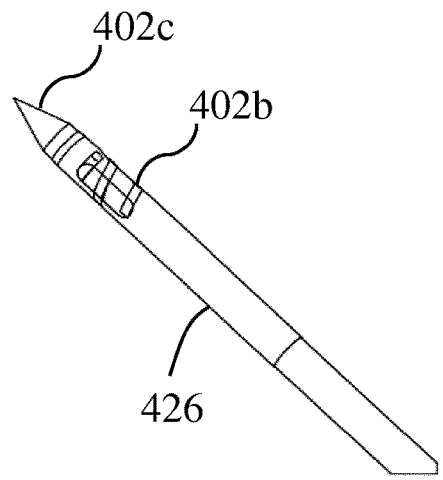
Figure 12a
Figure 12b

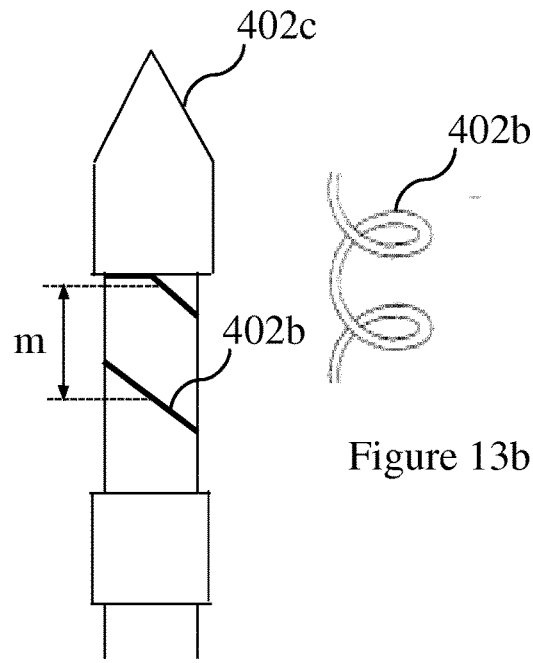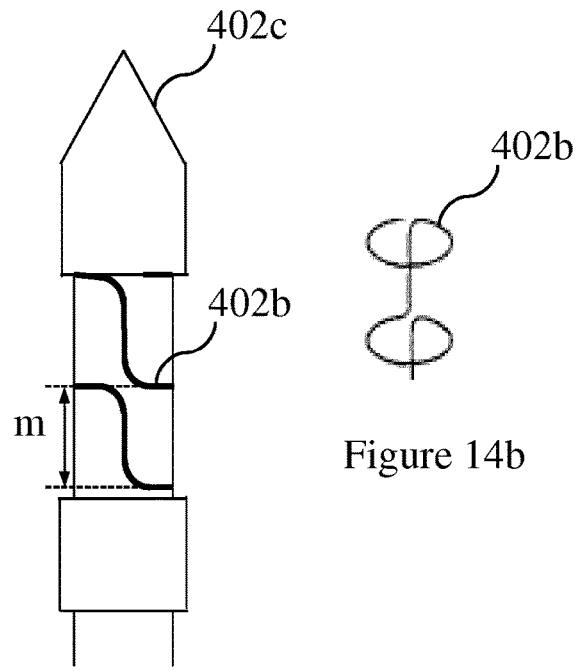
Figure 13b
Figure 13a
Figure 14b
Figure 14a
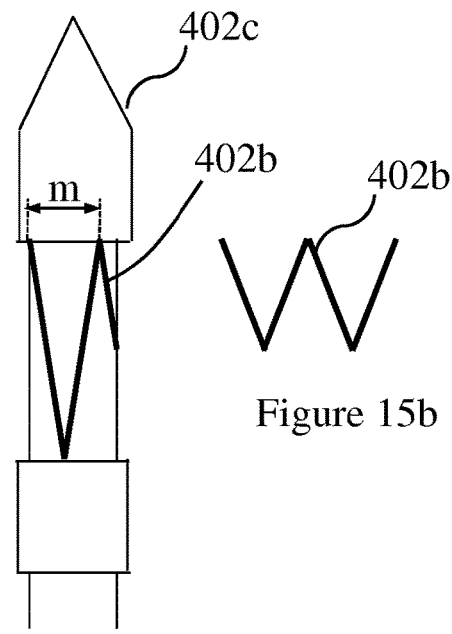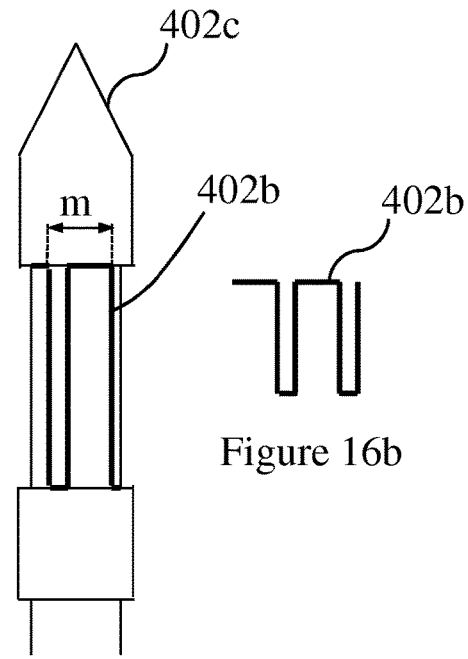
Figure 15b
Figure 15a
Figure 16b
Figure 16a

MICROWAVE ABLATION PROBE

This application relates to a microwave ablation probe. In particular, this application relates to an ablation probe that may be used to generate heat within tissue to destroy tissue growths.

Thermal ablation can be used to destroy tissue growths within the body which can be malignant. Current ablation systems use applicators that deliver Radio Frequency (RF) energy or microwave energy to the tissue surrounding an applicator tip. This causes localised heating and destruction of the malignant cells. These applicators may be designed for percutaneous delivery and are therefore relatively short in length and large in diameter. However, many disease locations cannot be safely or easily accessed percutaneously. For example, the location of the pancreas behind the liver makes it difficult to access percutaneously. Similarly, access to the lung through the chest wall can cause a pneumothorax. Large diameter applicators may also cause undesired tissue damage during insertion. This limits the range of indications where thermal ablation therapy can be successfully delivered using existing percutaneous applicators.

An endoscope can be used to access a number of disease locations that border the gastrointestinal tract. These include the pancreas, biliary tree, lymph nodes and a number of significant blood vessels. Furthermore, Endoscopic Ultrasound (EUS) systems provide a means of identifying lesions in tissue adjacent to the gastrointestinal tract using an ultrasound imaging system that is integrated within the endoscope. A biopsy needle can be delivered through the EUS system and directed to the target site under ultrasound guidance. Similar endoscopes are available to access disease locations in the lung using both ultrasound and navigation systems. This technology can be used to guide an extended working channel or steerable catheter to the disease location. Known applicator designs are not particularly suited for delivery through the working channel of an endoscope as they are typically too large in cross section and are of insufficient length and flexibility.

Prior art ablation probes comprise an active tip (or applicator) generally made of ceramic material which is coupled to a coaxial feed cable arranged to supply electromagnetic energy to the active tip. Where the feed cable is connected to the active tip a back current may be reflected back along the feed cable away from the active tip. This is particularly the case for microwave ablation. These currents can subtract power from the ablation zone around the applicator in the targeted tissue region and generate a tear-shaped ablation zone. A spherical ablation zone is however advantageous during use of the ablation probe in order to provide better control of the treatment being carried out.

A choke is a microwave component that is known to mitigate back currents running on the outer conductor of a feed cable supplying electromagnetic energy to an applicator or antenna. An example of a prior art choke is shown schematically in FIG. 1. In this example, a feed cable 102 is coupled to an active tip 104. The feed cable comprises an inner conductor 106 and an outer conductor 108. The inner conductor 106 can be seen extending into the active tip 104. In this example, the choke is formed by a metallic pocket 110 located at the base of the active tip 104. The choke generates image currents (labelled 'A') opposite in phase to the reflected current (labelled 'B') that help mitigate back currents on the outer conductor 108 of the feed cable.

There are a number of draw backs in using known chokes such as those shown in FIG. 1 with an ablation probe. The choke shown in FIG. 1 is not compact in size, and so may inhibit use of the ablation probe. The example choke shown in FIG. 1 is also difficult to keep cool using a flow of coolant without increasing the size of the device and may also inhibit the flexibility of the ablation probe.

In a first aspect, the present disclosure provides a microwave ablation probe, comprising: an applicator arranged to apply microwave radiation to heat surrounding tissue; a feeding cable arranged to supply electromagnetic energy to the applicator; a coolant flow path via which coolant is able to flow; and a choke arranged to reduce power reflected from the applicator along the feeding cable, wherein the choke comprises: a choke member cooled by coolant flowing in the coolant flow path, the choke member extending between two points spaced apart in a direction having at least a component parallel to a longitudinal axis of the feeding cable, the choke member comprising one or more turns extending around the longitudinal axis of the feeding cable.

Optionally, the choke member may comprise one or more curved portions extending around the longitudinal axis, the one or more curved portions being linked by one or more connecting portions extending in a direction having at least a component parallel to the longitudinal axis. Optionally the one or more curved portions may extend in a plane orthogonal to the longitudinal axis.

Optionally, the choke member is a spiral member. Optionally the spiral member forms a helix extending along the length of the feeding cable.

In a second aspect, the present disclosure provides a microwave ablation probe comprising one or more of the following features: an applicator arranged to apply microwave radiation to heat surrounding tissue; a feeding cable arranged to supply electromagnetic energy to the applicator; a coolant flow path via which coolant is able to flow; and a choke arranged to reduce power reflected from the applicator along the feeding cable, wherein the choke comprises: a spiral member cooled by coolant flowing in the coolant flow path.

By forming the choke from a component extending along the axis of the feeding cable and having one or more turns about that axis, an example of which being an at least partly spiral shaped component, it can be efficiently cooled without presenting a shape which would otherwise block or inhibit the flow of coolant. The choke member (e.g. the spiral shaped component) may also improve the flexibility of the ablation probe compared to a more rigid and solid prior art choke. The use of the choke member (e.g. the spiral member) may therefore provide an ablation probe which is small in cross section, flexible and efficiently cooled. The ablation probe may therefore reduce unwanted tissue damage during use and may be particularly advantageous when used with an endoscope to reach tissue via a tortuous route.

Optionally, the spiral member may form a helix extending along the length of the feeding cable. This may provide a shape suitable to allow the flow of coolant and provide the desired level of flexibility.

The features defined in any of the following statements can be used in combination with either the first or second aspect.

Optionally, the choke member (e.g. the spiral member) may be disposed at least partly within the coolant flow path. This may allow the choke member (e.g. the spiral member) to be cooled by coolant flowing through the ablation probe.

Optionally, the ablation probe may further comprise a first surrounding member arranged to at least partly surround the feeding cable, wherein the choke member (e.g. the spiral member) is disposed within the first surrounding member. This may help to provide a small and compact arrangement with a small cross section.

Optionally, the first surrounding member may comprise a tube arranged to surround the feeding cable. This may help create a needle portion of the ablation probe having a small and compact arrangement.

Optionally, the coolant flow path may comprise a feeding cable cooling portion comprising a channel formed between the feeding cable and the first surrounding member, and wherein the choke member (e.g. the spiral member) is arranged within the channel. This may provide a small and compact arrangement of the choke and coolant flow path while reducing the impact of the choke on the rate of flow of coolant.

Optionally, the coolant flow path may be arranged to provide a uniform flow of coolant around at least part of the length of the feeding cable and/or around the choke member (e.g. the spiral member). This may provide uniform cooling that may help provide controlled and repeatable ablation of tissue.

Optionally, the choke member (e.g. the spiral member) may be arranged to space apart an outer surface of the feeding cable and an inner surface of the first surrounding member to form the channel. This may help to stop the channel collapsing when the ablation probe is bent, and so may avoid constriction of the flow of coolant and may help reduce the chance of the ablation probe cracking or breaking.

Optionally, the choke member (e.g. the spiral member) may be arranged to concentrically align the feeding cable and the first surrounding member relative to each other. This may help to provide uniform cooling of the feeding cable and/or choke member (e.g. the spiral member).

Optionally, the choke member (e.g. the spiral member) may be arranged to electrically connect the first surrounding member to the feeding cable such that part of the first surrounding member forms part of the choke. This may allow the first surrounding member to provide both rigidity to the ablation probe and to act as part of the choke. This may help to provide an overall compact and small arrangement.

Optionally, the feeding cable may comprise an inner conductor and an outer conductor, and wherein the choke member (e.g. the spiral member) forms an electrical connection between the outer conductor of the feeding cable and the first surrounding member. This may allow part of the first surrounding member to form part of the choke.

Optionally, the electrical connection may be formed at a distance spaced along the length of the feeding cable from a distal end of the outer conductor. Optionally, the distance may be proportional to approximately a multiple of an odd number of one quarter of the wavelength of the electromagnetic energy corresponding to the operating frequency of the ablation probe. Optionally, the distance may correspond to approximately a multiple of an odd number of one quarter of the wavelength of the electromagnetic energy in a medium surrounding the feeding cable (e.g. the media within a choke region surrounding the feeding cable).

This may allow image currents in the choke to be provided which have the opposite phase to reflected current running back along the feeding cable.

Optionally, the pitch of the spiral member, or the axial separation of the one or more curved portions (i.e. in a direction along the longitudinal axis of the feeding cable) may be proportional to approximately one quarter of the wavelength of the electromagnetic energy corresponding to the operating frequency of the ablation probe. Optionally, the distance may correspond to approximately a multiple of an odd number of one quarter of the wavelength of the electromagnetic energy in a medium surrounding the feeding cable (e.g. the media within a choke region surrounding the feeding cable). This may further allow the desired phase of image current to be provided.

Optionally, the choke may comprise a choke region surrounding part of the feeding cable, the choke region being defined by the choke member (e.g. the spiral member) and at least part of the first surrounding member.

Optionally, the choke region may be at least partly filled with: a) coolant flowing in the coolant flow path; and/or b) a portion of the applicator arranged to extend between the feeding cable and the first surrounding member. This may allow the choke region to be filled with high permittivity media which may allow a reduction in the size of the choke.

Optionally, the first surrounding member may comprise a hinge portion, the hinge portion arranged to increase the flexibility of the first surrounding member. This may aid flexing of the ablation probe and help to reduce stress in the joint between the applicator and the feeding cable and/or the first surrounding member.

Optionally, the hinge portion may be arranged: a) between a proximal end of the applicator and a distal end of the choke member (e.g. the spiral member); and/or b) so as to overlap with at least part of the spiral member along the length of the feeding cable. This may allow the flexibility of the first surrounding member close to the applicator and/or around the choke member (e.g. the spiral member) to be controlled.

Optionally, the hinge portion may comprise one or weakened portions formed in the first surrounding member.

Optionally, the weakened portion(s) may be arranged to encourage flexing of the ablation probe. This may encourage the first surrounding member to flex at the position of the hinge portion in preference to at the coupling to the applicator (or at other undesirable points). This may help to reduce stress between components of the ablation probe.

Optionally, the hinge portion may be formed by one or more holes extending through the first surrounding member. Preferably the one or more holes may be arranged to allow coolant to flow. This may allow the hinge portion to both help control the flexibility of the ablation probe and to allow coolant to flow. This combined function may allow the overall size of the ablation probe to be reduced.

Optionally, the coolant flow path comprises an applicator cooling portion arranged to deliver a flow of coolant to at least part of the applicator. This may help to cool the applicator during ablation.

Optionally, the one or more holes forming the hinge portion may be arranged to fluidly couple the applicator cooling portion to a cable cooling portion of the coolant flow path.

Optionally, the ablation probe may comprise a second surrounding member arranged to surround at least part of the applicator and/or the first surrounding member, wherein the applicator cooling portion comprises a channel formed between the second surrounding member and one or both of the applicator and first surrounding member. This may provide a compact and small arrangement of the coolant flow path.

Optionally, the applicator cooling portion may comprise one or more channels in the surface or body of the applicator. This may also help provide a compact and small arrangement of the coolant flow path.

Optionally, the ablation probe may further comprise at least one temperature sensor. This may allow feedback to be provided on the temperature of the ablation probe during use and on the progress of the ablation.

Optionally, the at least one temperature sensor may comprise a thermocouple.

Optionally, the at least one temperature sensor may be integrated with, or is formed by, at least part of the choke member (e.g. the spiral member). This may allow the spiral member to act both as part of the choke and a temperature sensor.

Optionally, the applicator may comprise: an antenna portion of the inner conductor, the antenna portion extending from a distal end of the outer conductor; and an overlapping antenna member electrically coupled to the inner conductor, the overlapping antenna member may at least partly overlapping the antenna portion of the inner conductor along the length of the antenna portion of the inner conductor. This may allow a compact arrangement of the antenna to aid overall flexibility of the ablation probe, provide a more spherical ablation zone and aid cooling.

Optionally, the overlapping member may comprise one or more turns around the length of the antenna portion of the feeding cable. Optionally the geometry of the overlapping member may have a minimum spacing parameter, the minimum spacing parameter being greater than 0.05% of the wavelength of the radiation emitted by the applicator measured in air. This may reduce the effect of cancellation of signals within the parts of the antenna and so reduce loss of output signal strength.

Optionally, the applicator may further comprise a dielectric insulator, at least part of the dielectric insulator being disposed between the antenna portion of the inner conductor and the overlapping antenna member.

Optionally, the dielectric insulator may comprise an outer surface having a recessed portion, the recessed portion arranged to receive the overlapping antenna member. The depth of the recessed portion into the dielectric insulator may be adapted to combine mechanical strength and impedance matching of the applicator.

Optionally, the antenna portion of the inner conductor may extend from the distal end of the outer conductor a distance of between 0.3% and 10% of the wavelength of the microwave radiation emitted by the applicator measured in air.

Optionally, the overlapping antenna member may extend along the length of the antenna portion of the inner conductor a distance of between 0.3% and 20% of the wavelength of the microwave radiation emitted by the applicator measured in air.

Optionally, the overlapping antenna member may be cooled by coolant flowing in the coolant flow path.

Optionally, the applicator may further comprise a sleeve member, the sleeve member arranged to at least partly surround the overlapping antenna member to restrict the transfer of heat from the overlapping antenna member. This may reduce heat damage to other components of the ablation probe and may reduce tissue charring.

In a third aspect, the present disclosure provides a microwave ablation probe comprising one or more of the following features: an applicator arranged to apply microwave radiation to heat surrounding tissue; a feeding cable arranged to supply electromagnetic energy to the applicator; wherein the feeding cable is formed from an inner conductor and an outer conductor, wherein the applicator comprises: an antenna portion of the inner conductor, the antenna portion extending from a distal end of the outer conductor; and an overlapping antenna member electrically coupled to the inner conductor, the overlapping antenna member at least partly overlapping the antenna portion of the inner conductor along the length of the antenna portion.

Any features described above in connection with the first or second aspect may be used in combination with the third aspect.

Embodiments of the invention will now be described, by way of example only, with reference to the accompanying drawings, in which:

FIG. 2 shows a schematic cross section of part of an ablation probe according to an embodiment;

FIG. 3a shows a spiral member used in the ablation probe shown in FIG. 2;

FIG. 3b shows a choke member according to an alternative embodiment;

Figure 9A:
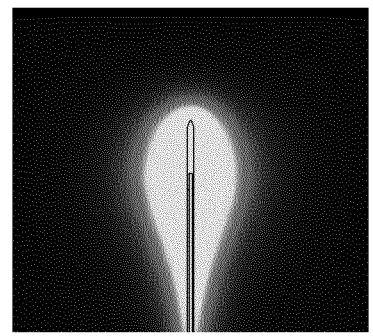
Figure 9B:
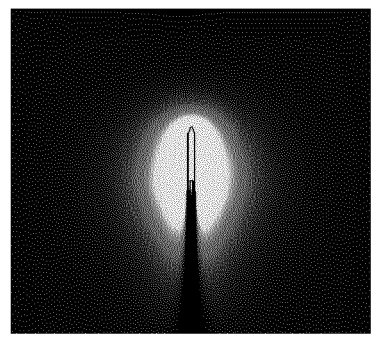
Figure 9C:
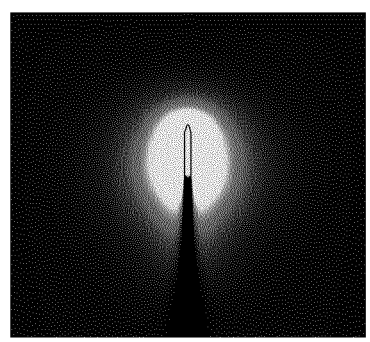
Figure 10A:
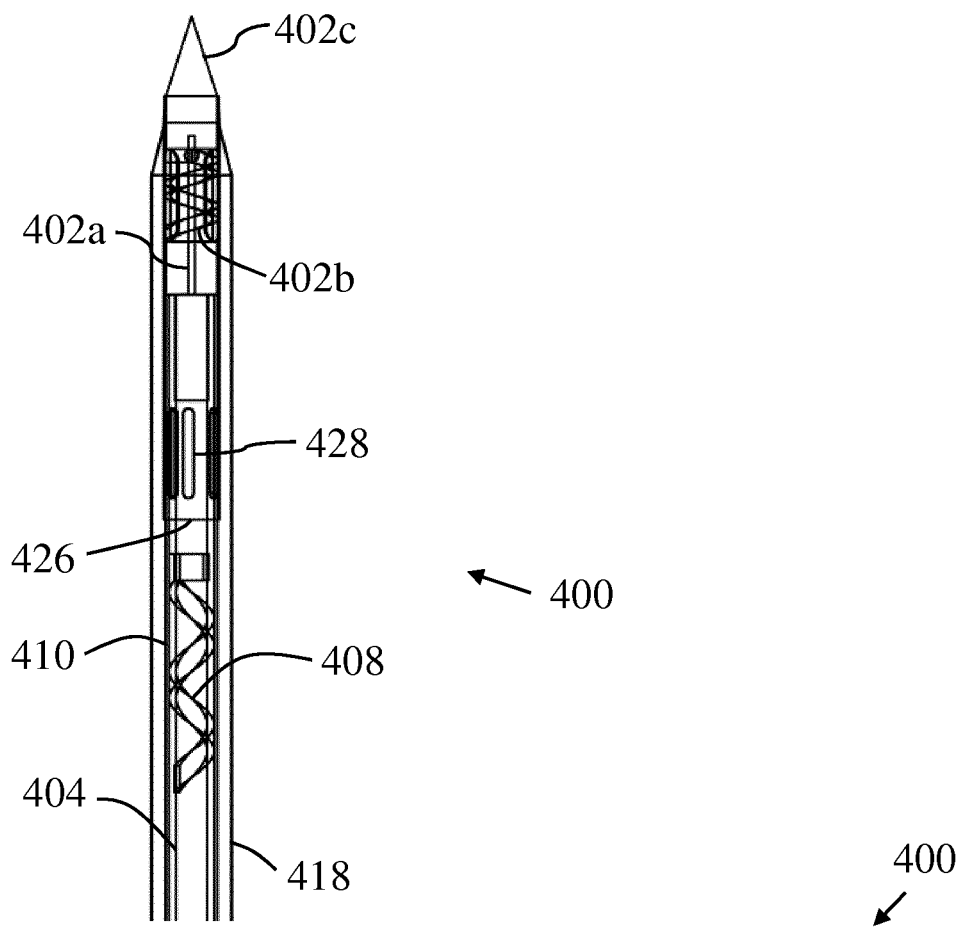
Figure 10B:
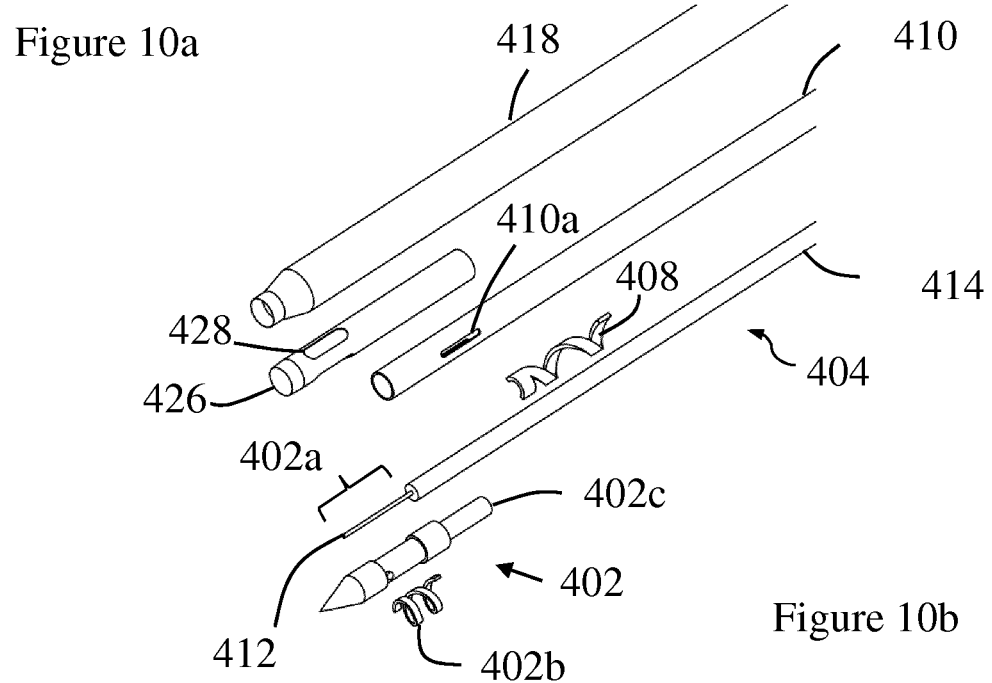

FIGS. 9a, 9b, and 9c show representations of the ablation zone produced by various ablation probes;

FIG. 10a shows a cross section view of part of an ablation probe according to another embodiment;

FIG. 10b shows an exploded view of the ablation probe shown in FIG. 10a;

FIG. 11a shows a close up view of part of the ablation probe shown in FIG. 10a;

FIG. 11b shows the same view as FIG. 11b with internal structures shown in broken lines;

FIG. 12a shows another exploded view of part of the ablation probe shown in FIG. 10a;

FIG. 12b shows an assembled view of the part of the ablation probe shown in FIG. 12a;

FIG. 13a shows a close up view of an embodiment of an overlapping member forming part of an applicator of the ablation probe;

FIG. 13b shows the overlapping member of FIG. 13a separately;

FIG. 14a shows a close up view of an embodiment of an overlapping member forming part of an applicator of the ablation probe;

FIG. 14b shows the overlapping member of FIG. 14a separately;

FIG. 15a shows a close up view of an embodiment of an overlapping member forming part of an applicator of the ablation probe;

FIG. 15b shows the overlapping member of FIG. 15a separately;

FIG. 16a shows a close up view of an embodiment of an overlapping member forming part of an applicator of the ablation probe; and FIG. 16b shows the overlapping member of FIG. 16a separately.

An ablation probe 200 according to one embodiment is shown schematically in FIG. 2. Only part of the overall length of the ablation probe is shown. The ablation probe 200 may be suitable for insertion into the body to reach a desired treatment site, such as a malignant tissue growth. In some embodiments, the ablation probe 200 may be used endoscopically in order to reach a variety of disease locations within the body. The ablation probe may therefore have an overall flexibility such that it can be inserted through the working channel of the endoscope. In other embodiments, the ablation probe 200 may also be used percutaneously, or using any other suitable technique, e.g. inserted through an existing aperture of the body. For percutaneous use, the ablation probe may be generally rigid so that it can be inserted.

The ablation probe 200 comprises an applicator 202 arranged to apply radiation to heat surrounding tissue. The applied radiation may be adapted to cause localised heating and destruction of malignant cells around or near to the applicator 202. In the described embodiment, the applicator 202 is arranged to apply microwave radiation to surrounding tissue. In some embodiments, the operating frequency may be around 2.45 GHz. In other embodiments, the operating frequency may vary from this value within the microwave range. In other embodiments, the applicator 202 may be arranged to apply any suitable form of radiation to surrounding tissue such that the desired heating is caused (e.g. RF radiation). In the described embodiment, the applicator may be formed from a ceramic material. In other embodiments, other suitable materials may be used (e.g. any suitable dielectric material or other type of antenna material or structure). The applicator 202 may be arranged at or near a distal end of the ablation probe 200 so that it can be positioned in a desired position relative to the tissue to be treated. In the following, the terms "distal" and "proximal" are taken relative to the user operating the ablation probe and the treatment site when the ablation probe is positioned for use—the distal end of the ablation probe 200 is that closest to the treatment site and the proximal end is that closest to the user. A control means (not shown in the Figures) such as a handle may be provided at the proximal end of the ablation probe 200 so that it can be manipulated and positioned by the user.

The ablation probe 200 further comprises a feeding cable 204 which is arranged to supply electromagnetic energy to the applicator 202. The feeding cable 204 may be any elongate member suitable for supplying electromagnetic energy to the applicator (e.g. a conductor). The feeding cable 204 may run along at least part of the length of the ablation probe 200 to deliver a supply of energy to the applicator 202. In the described embodiment, a distal end of the feeding cable 204 is coupled to a proximal end of the applicator 202 and a proximal end of the feeding cable 204 is coupled to a generation means (not shown in the Figures) suitable for generating the desired signal to supply energy to the applicator 202 (i.e. the full length of the feeding cable is not shown in the Figures).

The ablation probe 200 further comprises a coolant flow path 206 via which coolant is able to flow. The coolant flow path may be arranged to carry coolant through the ablation probe 200 to provide cooling. The coolant flow path 206 may comprise different portions arranged to deliver and return coolant to and from various parts of the ablation probe as will be described later. The coolant may be water, or any other suitable coolant known in the art.

The ablation probe 200 further comprises a choke arranged to reduce power reflected from the applicator 202 along the feeding cable 204. The choke is arranged to create an image current which acts to at least partly cancel out currents reflected from the applicator 202 along the feeding cable 204. The image currents may be opposite in phase to those that would be reflected back along the feeding cable so that they produce electromagnetic fields which combine to at least partly cancel each other out. The image currents and reflected currents are opposite in phase to each other so that they at least partly cancel each other out. In terms of impedance, this corresponds to a very high impedance condition at the choke that reduces or prevents currents flowing back along the feeding cable. The choke comprises a spiral member 208 which is cooled by coolant flowing in the coolant flow path 206. An embodiment of the spiral member 208 is shown separately from the ablation probe in FIG. 3. As can be seen in the figures, the spiral member 208 comprises a component at least part of which has a spiral shape.

The choke may be positioned so that it is cooled by the coolant flowing along the coolant flow path 206 towards the applicator 202. This means that the choke may be cooled by the flow of coolant that is otherwise required to cool various parts of the ablation probe 200 as will be described later.

By forming the choke at least partly from the spiral member 208 a number of advantages are provided over prior art chokes. The spiral member 208 may be more efficiently cooled by coolant flowing in the coolant flow path 206 as its spiral shape provides a large surface area for cooling. The spiral shape of the spiral member 208 may also reduce any impact on the flow of coolant even when the spiral member 208 is packaged within the body of the ablation probe 200 to provide a compact overall size (e.g. the spiral shape may allow coolant to easily flow around it without forming a solid block which may impede the flow of coolant within the ablation probe 200). The spiral shape of the spiral member 208 may also provide improved flexibility of the ablation probe 200. Prior art chokes may be a solid construction and are therefore more rigid and so may inhibit the flexing of the ablation probe during use. This is particularly important in embodiments where the ablation probe is to be used in conjunction with an endoscope used to access difficult to reach parts of the body. In such an embodiment, the improved flexibility of the spiral member 208 allows the ablation probe 200 to pass through a tortuous route to the desired ablation site within the body.

As can be seen in FIGS. 2 and 3a, the spiral member 208 forms a helix extending along the length of the feeding cable 204. In the described embodiment, the spiral member 208 is disposed within the coolant flow path 206 so that it is cooled by the flow of coolant. In other embodiments, the spiral member 208 may be only at least partly disposed within the coolant flow path 206. This shape and arrangement allows a compact design to be achieved so as to reduce the cross section of the ablation probe 200, without inhibiting the flow of coolant within the ablation probe 200 and the cooling of the choke. In the described embodiment, at least part of the spiral member may have a single helical shape. In other embodiments, at least part of the spiral member may have a double helical shape, a triple helical shape or may be formed by any number of connected or interwoven helical shaped portions. The spiral member may be formed from either a right-handed or left-handed spiral as appropriate.

In the embodiment shown in FIG. 3a, the spiral member 208 may form a curved helical path. In other embodiments, the spiral member 208 may have one or more straight sections. In that case, it will still however follow a generally spiralled path around and along the feeding cable 204.

The spiral member 208 is only one example of a choke member that may be used to reduce signals reflected back along the feeding cable. In other embodiments, a choke member having a differing geometry may be used. The choke may comprise a choke member extending between two points (labelled A and B in FIGS. 2, 3a and 3b) that are spaced apart in a direction parallel to a longitudinal axis (labelled Y in FIG. 2) of the feeding cable, the choke member comprising one or more turns extending around the longitudinal axis of the feeding cable. FIGS. 2 and 3a therefore show an example of a choke member extending between points A and B, with one or more turns around the longitudinal axis Y between them. The alternative embodiment of the choke member shown in FIG. 3b similarly extends between points A and B, with one or more turns around the longitudinal axis Y between them.

The turns of the choke member allow suppression of a current reflected back along the feeding cable from the application, while also providing a flexible structure which can be efficiently cooled. The choke member may therefore define a continuous coolant channel which extends between the two points defined above between which the choke member extends.

The spiral member is an example of the choke member in which the turns are joined to form a continuous spiral or helix extending along the length of the feeding cable.

In another embodiment, the choke member may comprise one or more curved portions that extend in a plane (labelled X in FIG. 2) orthogonal to the longitudinal axis. The one or more curved portions may be linked by one or more connecting portions extending in a direction parallel to the longitudinal axis. An example of this is shown in FIG. 3b. In this embodiment, the choke member 209 comprises a plurality of curved portions 209a extending around the feeding cable. The curved portions 209a may extend only partly around the feeding cable (e.g. at least half a turn around the feeding cable). This may allow the flow of coolant around and through the choke member. The curved portions 209a are connected via one or more connecting portions 209b extending in a direction having at least a component along the length of the feeding cable 204. The connecting portions 209a may be generally straight as shown in FIG. 3b. The curved portions 209a may be spaced apart along the length of the feeding cable to allow image currents to form within the curved portions that will act to cancel out current reflected along the feeding cable from the applicator. The spacing of the curved portions 209a may be the same as the spacing between corresponding points of the spiral member along the length of the feeding cable as will be described later (e.g. distance C in FIG. 2).

Any other feature mentioned herein with respect to the spiral member 208 may apply equally to other embodiments of the choke member. The spiral member 208 of any embodiment described may therefore be replaced by a choke member having the geometry defined above, e.g. the choke member shown in FIG. 3b.

The choke member may be formed from an elongate component following a path running at least partly around the longitudinal axis of the feeding cable. In the case of the choke member 209 shown in FIG. 3b, each curved portion 209a extends in a plane (labelled X in FIG. 2) perpendicular to the longitudinal axis (labelled Y in FIG. 2) of the feeding cable. Each curved portion therefore extends around, but not along, the length of the feeding cable. The spiral member extends such that it is formed from curved portions that are angled relative to a plane perpendicular to the longitudinal axis of the feeding cable such that it extends around and along the feeding cable (i.e. it spirals along its length). In yet another embodiment, the curved portions may be angled relative to the plane orthogonal to the longitudinal axis, but also linked by one or more connecting portions extending parallel to the longitudinal axis.

Both the spiral member 208 (or other example of the choke member) may be formed from any suitable electrically conducting material such that it may act as a choke by carrying a suitable image current. The spiral member 208 or other example of the choke member may, for example, be formed from a metal. In some embodiments, the choke member 208, 209 may be formed from a separate component, or may be formed by depositing or plating material onto a suitable structure of the ablation probe (e.g. around the feeding cable).

In some embodiments, the spiral member may comprise a locating portion 208a comprising a surface generally perpendicular to a longitudinal axis of the spiral member (e.g. an axis of the the helix forming the spiral member). The locating proportion may provide a more distinct reference from which the spiral member is to be spaced apart from the applicator or distal end of the feeding cable as described later. This may allow more accurate positioning of the spiral member during assembly. In the described embodiment, the locating portion is formed by a portion of the spiral member having a tubular shape extending at least part way around the longitudinal axis of the spiral member.

The ablation probe 200 may further comprise a surrounding member 210 arranged to at least partly surround the feeding cable 204. The surrounding member may comprise a tube (e.g. a hypotube), as shown in the cross section view of FIG. 2, which is arranged to completely surround the feeding cable 204. In other embodiments, the surrounding member 210 may be any other suitable shape and may only partly surround the feeding cable 204. The spiral member 208 (or other example of the choke member) may be disposed within the surrounding member 210 (e.g. it is within the hollow body of the tube). This may provide a small and compact arrangement.

The tube (or other shaped component) forming the surrounding member 210 may act to form a needle portion of the ablation probe 200 that can be inserted into tissue during use. In this embodiment, the tube may have a rigidity sufficient to allow insertion into tissue, but may also be sufficiently flexible to allow it to bend and to be used in an endoscope. In some embodiments, a rigid surrounding member may be provided to allow percutaneous use of the ablation probe where flexibility is not so important. In some embodiments, the tube forming the surrounding member 210 may be formed from NiTi alloy (Nitinol). This may provide a suitable level of flexibility and electrical conductivity.

In some embodiments (not shown in the figures) the ablation probe 200 generally comprises two portions: the needle portion and a catheter portion. The needle portion may be arranged at the distal end of the ablation probe 200 and is adapted to be inserted into tissue during use to reach the desired ablation location. The needle portion may comprise the applicator 202, a distal part of the feeding cable 204, the spiral member 208 and the surrounding member 210 as discussed above. The catheter portion may be provided at the proximal end of the ablation probe 200 and is arranged to supply electromagnetic energy and a flow of coolant to and from the needle portion. In some embodiments, the ablation probe 200 may further comprise a handle portion via which the ablation probe 200 may be manipulated and positioned during use. The catheter portion may have an extended length and flexibility for endoscopic use. In other embodiments, a shorter, more rigid catheter portion may be provided for percutaneous use.

In some embodiments, the needle portion may form a small part of the overall length of the ablation probe 200. For example, the needle portion may be approximately 5 mm to 2000 mm in length, and preferably may be around 70 mm in length. The length of the needle portion may be chosen according to the anatomy to be accessed. A length of around 70 mm may be advantageous for providing good access to ablation sites in the pancreas. A longer length of needle portion may be more suitable for accessing parts of the lung, for example. The catheter portion may be around 1000 mm to 2000 mm in length, and preferably around 1400 mm in length. The length of the catheter portion may be chosen according to the position of the ablation site which must be reached. In other embodiments, the needle portion of the ablation probe 200 may form a greater proportion of the overall length of the ablation probe. In some embodiments, the entire length of the ablation probe 200 may be formed by the needle portion. In such an embodiment, the catheter portion may not be required. For example, if the ablation probe is to be used percutaneously the catheter portion may be shorter than for endoscopic use, or may not be required.

In some embodiments, the coolant flow path 206 may comprise a feeding cable cooling portion arranged to provide cooling to at least part of the feeding cable 204. The feeding cable cooling portion may comprise a channel formed between the feeding cable 204 and the surrounding member 210. In the described embodiment, the surrounding member 210 is formed from a tube extending around the feeding cable 204 to form a channel between them. In this embodiment, the inner diameter of the tube is greater than the outer diameter of the feeding cable 204 to create a gap between them along which cooling fluid may flow. This arrangement may provide direct and efficient cooling of the feeding cable 204 along the part of its length surrounded by the tube. In other embodiments, alternative geometries may be provided and the channel forming the feeding cable cooling portion may have a different shape. For example, the tube may be oval or square in cross section. In other embodiments, the surrounding member 210 may surround only part of the feeding cable 204 so as to form one or more separate channels running along the outside of the feeding cable 204.

In some embodiments, the surrounding member 210 may comprise one or more holes or slots through which coolant may flow out of the feeding cable cooling portion. The holes or slots may be arranged at or near the distal end of the surrounding member.

The spiral member 208 may be arranged within the channel forming the cable cooling portion of the cooling flow path. This may allow the spiral member 208 (or other example of the choke member) to be efficiently cooled by the coolant. As discussed above, the shape of the spiral member 208 (or other example of the choke member) may allow coolant to flow around it so as to reduce any effect on the rate of flow along the coolant flow path 206.

In the described embodiment, the coolant flow path 206 is arranged to provide a uniform flow of coolant around at least part of the length of the feeding cable 204. As can be seen in FIG. 2, the feeding cable portion of the coolant flow path forms a uniform layer of coolant flowing around the feeding cable 204. In this embodiment, the spiral member 208 (or other example of the choke member) may also be located within the feeding cable cooling portion and so is also provided with a uniform flow of coolant. By providing a uniform flow of coolant around the feeding cable 204 and/or spiral member 208 (or other example of the choke member) their temperature may be more reliably controlled. This may help to achieve regular and repeatable ablation of surrounding tissue.

The spiral member 208 (or other example of the choke member) may be arranged to space apart an outer surface of the feeding cable 204 and an inner surface of the surrounding member 210 to form the channel. The spiral member (or other example of the choke member) may therefore provide a coupling between the feeding cable 204 and the surrounding member 210 so as to set the separation between them and maintain the shape of the channel. This may help to prevent the channel from collapsing when the ablation probe 200 flexes and so may help maintain the flow of coolant.

In some embodiments, the spiral member 208 (or other example of the choke member) may be arranged to concentrically align the feeding cable 204 and the surrounding member 210 relative to each other. The concentric alignment may provide a uniform flow of cooling fluid in the channel around the feeding cable 204 to provide uniform cooling. In other embodiments, the spiral member 208 (or other example of the choke member) may be arranged to maintain the feeding cable 204 in a fixed position relative to the surrounding member 210 in a non-concentric arrangement (e.g. the feeding cable 204 may not run down a central longitudinal axis of the tube forming the surrounding member).

The spiral member 208 (or other example of the choke member) may be arranged to electrically connect the surrounding member 210 to the feeding cable 204 such that part of the surrounding member 210 forms part of the choke. The spiral member 208 (or other example of the choke member) may therefore act to transmit a current carried by the feeding cable 204 to the surrounding member 210. This allows out of phase currents to be set up in the surrounding member 210 which act to at least partly cancel out any current reflected by the applicator 202 back along the feeding cable 204.

By forming the choke from the spiral member 208 (or other example of the choke member) and a portion of the surrounding member 210 a separate choke component may not be required.

This may help provide a small and compact choke arrangement. The choke shown in FIG. 2 comprises a choke region (or pocket) surrounding the feeding cable 204. The choke region is defined by the spiral member 208 (or other example of the choke member) and at least part of the surrounding member 210 which form the choke. As can be seen in FIG. 2, the choke region may be at least partly filled by coolant flowing in the coolant flow path.

Figure 5:
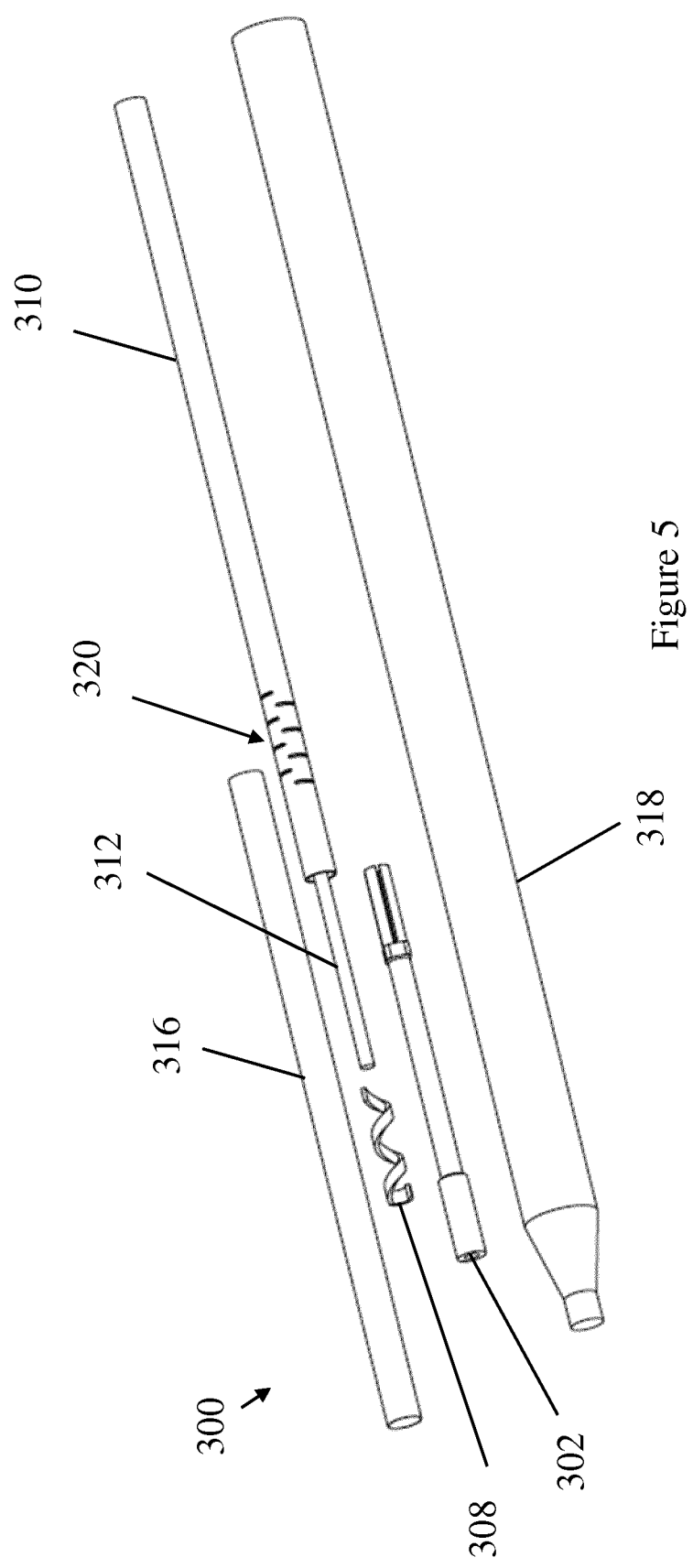
FIG. 5 shows an exploded view of part of an ablation probe according to an embodiment.

In some embodiments, as shown in FIG. 2, a portion of the applicator 202 may be arranged to extend between the feeding cable 204 and the surrounding member 210. This portion of the applicator 202 may therefore at least partly fill the choke region. In some embodiments (e.g. as shown in FIG. 5), the portion of the applicator extending between the surrounding member and the feeding cable may be divided into one or more finger members. This may aid flexibility. The finger members may also align with the slots in the surrounding member to allow coolant to flow along the coolant flow path.

By including coolant and/or part of the applicator material (e.g. formed by a ceramic material) within choke region the permittivity of the choke region may be increased (in comparison to if it was filled with air, for example). This may allow the overall size of the choke to be reduced. This is because the size of the choke region required to provide the desired image current is proportional to the square root of the permittivity of the media inside it. By filling the choke region with coolant and/or part of the applicator 202 the overall cross sectional size of the ablation probe 200 may be reduced.

In the described embodiment, the feeding cable 204 comprises an inner conductor 212 and an outer conductor 214. The inner conductor 212 may be separated from the outer conductor 214 by a dielectric material shown by the shaded region between them in FIG. 2. The inner conductor 212 may extend into the body of the applicator 202, and so may extend beyond a distal end of the outer conductor 214 (and the dielectric). The applicator is therefore formed from the portion of the inner conductor extending from the outer conductor and the ceramic material to form a monopole antenna. In some embodiments, the feeding cable may therefore be formed from a coaxial cable. In other embodiments, a different coupling between the feeding cable 204 and the applicator may be provided.

The spiral member 208 (or other example of the choke member) may form an electrical connection between the outer conductor 214 of the feeding cable 204 and the surrounding member 210. In some embodiments, the spiral member 208 (or other example of the choke member) may be electrically connected along all of its length to the surrounding member 210. In such an embodiment, an inside surface of the spiral member (labelled 208b in FIG. 3), or other example of the choke member, may form an electrical contact with the outer surface of the feeding cable 204. An outside surface 208c of the spiral member 208 may form an electrical contact with an inner surface of the surrounding member 210. This connection may also act to set the separation between the feeding cable 204 and the surrounding member 210. In other embodiments, the spiral member 208 (or other example of the choke member) may be electrically connected to the surrounding member 210 at just one or more discrete points along its length. For example, at least one turn of the spiral member 208 (or other example of the choke member) may be electrically coupled to the feeding cable 204 and/or the surrounding member 210.

In some embodiments, the electrical connection formed between the spiral member 208 (or other example of the choke member) and the surrounding member 210 may be at a distance spaced along the length of the feeding cable 204 from a distal end of the outer conductor 214. The distance may be arranged so that the current flowing from the outer conductor 214 to the choke has the desired phase to cancel out any current reflected by the applicator 202. The separation distance is labelled 'C' in FIG. 2. In some embodiments, the distance C may be proportional to approximately a multiple of an odd number of one quarter of the wavelength of the electromagnetic energy corresponding to the operating frequency of the ablation probe when operating in the microwave range. In the described embodiment, the distance C may be proportional to approximately one quarter of the wavelength of the operating frequency. This separation may create the desired phase difference between current flowing through the spiral member 208 and first surrounding portion 210 forming the choke and a current reflected along the outer conductor 214 from the applicator 202.

The spacing of the electrical connection between the spiral member 208 (or other example of the choke member) and surrounding member 210 from the distal end of the outer conductor 214 (i.e. distance C) may be determined by the permittivity of the media surrounding the feeding cable within that distance. In some embodiments, the distance C shown in FIG. 2 may be about $n\lambda_m/4$, where $\lambda_m$ refers to the wavelength of electromagnetic energy in the medium filling the choke region defined above, and n is an integer. In this expression, $\lambda_m = \lambda/\sqrt{\varepsilon_m}$ where $\varepsilon_m$ is the permittivity of the medium filling the choke region and $\lambda$ is the wavelength of the operating frequency of the ablation probe.

In some embodiments, the pitch of the spiral member 208 (e.g. the pitch of a helix formed by the spiral member 208) may be proportional to approximately one quarter of the wavelength of the electromagnetic energy corresponding to the operating frequency of the ablation probe 200. In other embodiments, the distance along the length of the feeding cable between the one or more curved portions 209a forming the choke member 209 may be proportional to approximately one quarter of the wavelength of the electromagnetic energy corresponding to the operating frequency of the ablation probe 200. The pitch of the spiral member (or curved portion 209a spacing) may also be determined by the permittivity of the media surrounding the feeding cable (e.g. maybe the same as distance C defined above). This may produce a repeating electrical contact between the feeding cable 204 and the surrounding member 210 at approximately one quarter wavelength intervals (as shown by the repeating distance C labelled in FIG. 2). In other embodiments, the pitch of the spiral member 208 (or curved portion 209a spacing) may vary from this amount, and may vary along the length of the spiral member 208 (or other example of the choke member).

Another embodiment of an ablation probe 300 according to an embodiment of this disclosure is shown in FIGS. 4 to 6d. The embodiment shown in the Figures is to be understood as only one example. Features in FIGS. 4 to 6d that are common to the embodiment of FIG. 2 are labelled accordingly.

The ablation probe 300 shown in FIGS. 4 to 6d generally comprises an applicator 302, a feeding cable 304, a spiral member 308 and a first surrounding member 310. The spiral member shown in FIG. 4 may be replaced by a choke member according to any other embodiment described herein. The feeding cable 304 comprises an inner conductor 312 and an outer conductor 314. In this embodiment, the ablation probe 300 further comprises a second surrounding member 316, a deformable member 318 and a hinge portion 320 as will be described in more detail below. Any of the features described above in connection with the embodiment shown in FIGS. 2 and 3 may also be used in the embodiment shown in FIGS. 4 to 6d, and vice versa.

Figure 4:
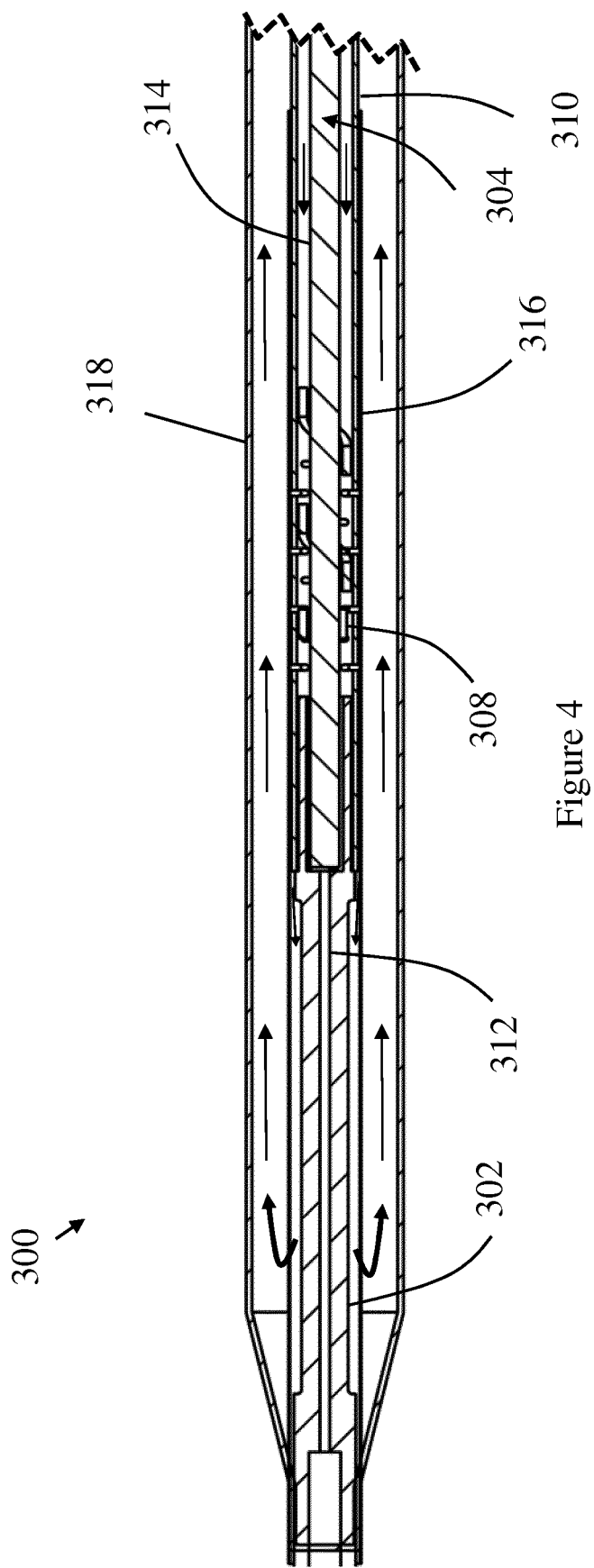
FIG. 4 shows a cross section view through part of an ablation probe according to an embodiment.

FIG. 4 shows a cross section through part of the ablation probe 300 along its length from its proximal end to its distal end. FIG. 5 shows an exploded view of part of the ablation probe 300. FIGS. 6a to 6d show the ablation probe 300 in various phases of assembly. In FIG. 6a the feeding cable 304 has been inserted into the applicator 302 and the spiral member 308 fitted around the feeding cable 304. In FIG. 6b the first surrounding member 310 has been fitted around the feeding cable 304 so that it is spaced apart from it by the spiral member 308. In FIG. 6c the second surrounding member 316 has been fitted around the first surrounding member 310 and the applicator 302 as will be described later. Finally, in FIG. 6d the deformable member 318 has been fitted around the first and second surrounding members.

The coolant flow path of the ablation probe 300 may comprise a feeding cable cooling portion, an ablation probe cooling portion and a return portion. The arrows shown in FIG. 4 indicate the direction of the flow of coolant along the coolant flow path. In this embodiment, the coolant flows along the feeding cable cooling portion to provide cooling along (at least part of) its length. As described above, the spiral member 308 forming part of the choke may be disposed within the feeding cable cooling portion so that it is also cooled. The feeding cable cooling portion may extend along the length of the feeding cable 304 until a point at or near the applicator 302 as shown in FIG. 4. In other embodiments, the feeding cable cooling portion may stop before this point.

In the described embodiment, the feeding cable cooling portion is fluidly coupled to an applicator cooling portion. The applicator cooling portion may be fluidly coupled to the feeding cable cooling portion at a point downstream of the spiral member 308. This means that the coolant must flow past or around the spiral member 308 in order to reach the applicator cooling portion. The spiral shape of the spiral member 308 is therefore advantageous because it helps to reduce constriction of the rate of flow of coolant through the feeding cable portion, and then to the applicator cooling portion, while not requiring the overall cross section of the ablation probe 300 to be increased.

The applicator cooling portion may cool the applicator by extending along part or all of the length and width of applicator 302. The applicator cooling portion may be formed by any one of more of: a channel formed between the second surrounding member 316 and the applicator 302, one more channels in the surface of the applicator 302; and one or more channels formed in the body of the applicator 302.

In the embodiment shown in FIGS. 4 to 6d, the applicator cooling portion comprises a channel formed by the second surrounding member 316. The second surrounding member may surround at least part of the length of the first surrounding member and at least part of the length of the applicator to form a channel in which coolant can flow. One or more holes may be formed in the first surrounding member to fluidly couple the applicator cooling portion to the cable cooling portion of the coolant flow path. In the described embodiment, the second surrounding member 316 comprises a tube arranged to surround part of the applicator 302 and part of the first surrounding member 310. The second surrounding member 316 may be spaced apart from the body of the applicator 302 (or at least part of it, as shown in FIG. 4) to define a coolant channel between them. In some embodiments, the second surrounding member 316 may be formed by a polyamide material which is arranged to resist the heat generated by the applicator 302.

In other embodiments, the applicator cooling portion may comprise one or more slots in the outer surface of the applicator 302. In such an embodiment, the slots may be closed off by the second surrounding member 316 to form one or more individual channels along which coolant may flow. In yet other embodiments, the applicator cooling portion may be formed by one or more channels disposed within the body of the applicator 302. In such an embodiment, the second surrounding member 316 may not be required. In such an embodiment, the channels in the applicator 302 may be fluidly coupled directly to the feeding cable cooling portion of the coolant flow path.

The applicator cooling portion may be fluidly coupled to a return portion of the coolant flow path. The coolant may therefore flow along the return portion towards the proximal end of the ablation probe 300. It may then be returned to a pump and cooling means so as to be recirculated through the coolant flow path, or allowed to leave the system and replaced by new coolant, as would be apparent to the skilled person.

In some embodiments, the feeding cable cooling portion may be fluidly coupled directly to the return portion. In such an embodiment, the applicator cooling portion may not be present, or coolant may at least partly bypass the applicator cooling portion to flow straight back along the return portion.

In the embodiment shown in FIGS. 4 to 6d, the coolant return portion is formed by a deformable member arranged to move between an insertion configuration in which insertion of the ablation probe 300 is facilitated and a deployed configuration. The coolant return portion may be created by space between a wall of the deformable member and the body of the ablation probe when it is in the deployed configuration. This may allow the cross sectional size of the ablation probe 300 to be reduced during insertion when the flow of coolant is not required. In the embodiment shown in FIGS. 4 to 6d, the deformable member 318 may comprise an inflatable member (e.g. a balloon) that surrounds at least part of the first surrounding member 310, at least part of the second surrounding member 316 and at least part of the applicator 302. In other embodiments, the deformable member 318 may have any other suitable shape to provide a return path for coolant flowing from the feeding cable cooling portion and/or the applicator cooling portion. For example, the deformable member 318 may extend only part of the way around the inner parts of the ablation probe 300, or may be formed by one or more separate deformable members extending along its length. In other embodiments, the deformable member may be replaced by a non-deformable member that may define the coolant return portion along some, or all, of the length of the ablation probe 300. In this embodiment, a fixed shaped channel for the coolant return portion may be provided.

In the described embodiment, the coolant return portion may be arranged so that it is further away from the feeding cable 304 and the applicator 302 compared to the feeding cable cooling portion and/or the applicator cooling portion. In the described embodiment, the return portion is disposed (at least partly) around the outside of the feeding cable cooling portion and/or the applicator cooling portion. This means that the flow of coolant travelling along the coolant flow path from the proximal end to the distal end of the ablation probe 300 runs closer to the feeding cable 304 and/or applicator 302 compared to the returning coolant flowing in the opposite direction along the return portion. This may help to provide a flow of colder coolant to the parts of the applicator 300 that require high levels of cooling. The arrangement of the coolant flow path shown in the Figures is however only one such example and other arrangements are possible. A different arrangement of coolant channels may be provided in other parts of the ablation probe (e.g. a catheter portion as described above). In some embodiments, the direction of the flow of coolant shown in FIG. 4 may be reversed.

The ablation probe 300 may further comprise a hinge portion 320 arranged to increase the overall flexibility of the ablation probe. In the described embodiment, the first surrounding member 310 may comprise the hinge portion 320. The hinge portion 320 may be arranged between a proximal end of the applicator 302 and a distal end of the spiral member 308. The hinge portion 320 may be further or alternatively arranged to overlap with at least part of the spiral member 308 along the length of first surrounding member 310. This arrangement may help to increase flexibility of the first surrounding member 310 around the spiral member 308 and/or close to the applicator 302. This may help to decouple stress forces created in the first surrounding member 310 from the applicator 302 when the ablation probe 300 is bent during use.

The hinge portion 320 may comprise one or weakened portions formed in the first surrounding member 310. The weakened portions may be arranged to encourage flexing of the ablation probe 300 at a certain point along its length. For example, the size, shape and/or orientation of the weakened portion(s) may encourage bending of the ablation probe 300 at the location of the hinge portion 320. This may improve the flexibility of the ablation probe 300 and allow it to bend around tortuous anatomy and may allow it to be more easily used with an endoscope. The hinge portion 320 may however be arranged to still provide adequate stiffness of the ablation probe so as not to compromise its column strength and/or to allow sufficient pushabilty so that it can pierce tissue during use.

By providing the hinge portion 320 at a specific point along the first surrounding member 320 the stress on the applicator 302 may be reduced. The ablation probe may flex preferentially at the hinge portion 320, rather than at the point of connection between the applicator and first surrounding member 310. This may help to reduce stress on the applicator 302.

The hinge portion 320 may comprise one or more transverse slots extending through a wall of the first surrounding member 310. By extending perpendicularly to the length (e.g. from the distal to proximal ends) of the first surrounding member 310 the hinge member 320 may be arranged to encourage bending along the length of the ablation probe (e.g. bending away from being straight along its longitudinal axis from the distal to proximal end). The hinge portion 320 may be arranged to extend uniformly around the first surrounding member 310 to allow even flexing in all directions. In other embodiments, the hinge member 320 may extend only part way around the first surrounding member 310 to encourage flexing in only certain directions.

Figure 6:
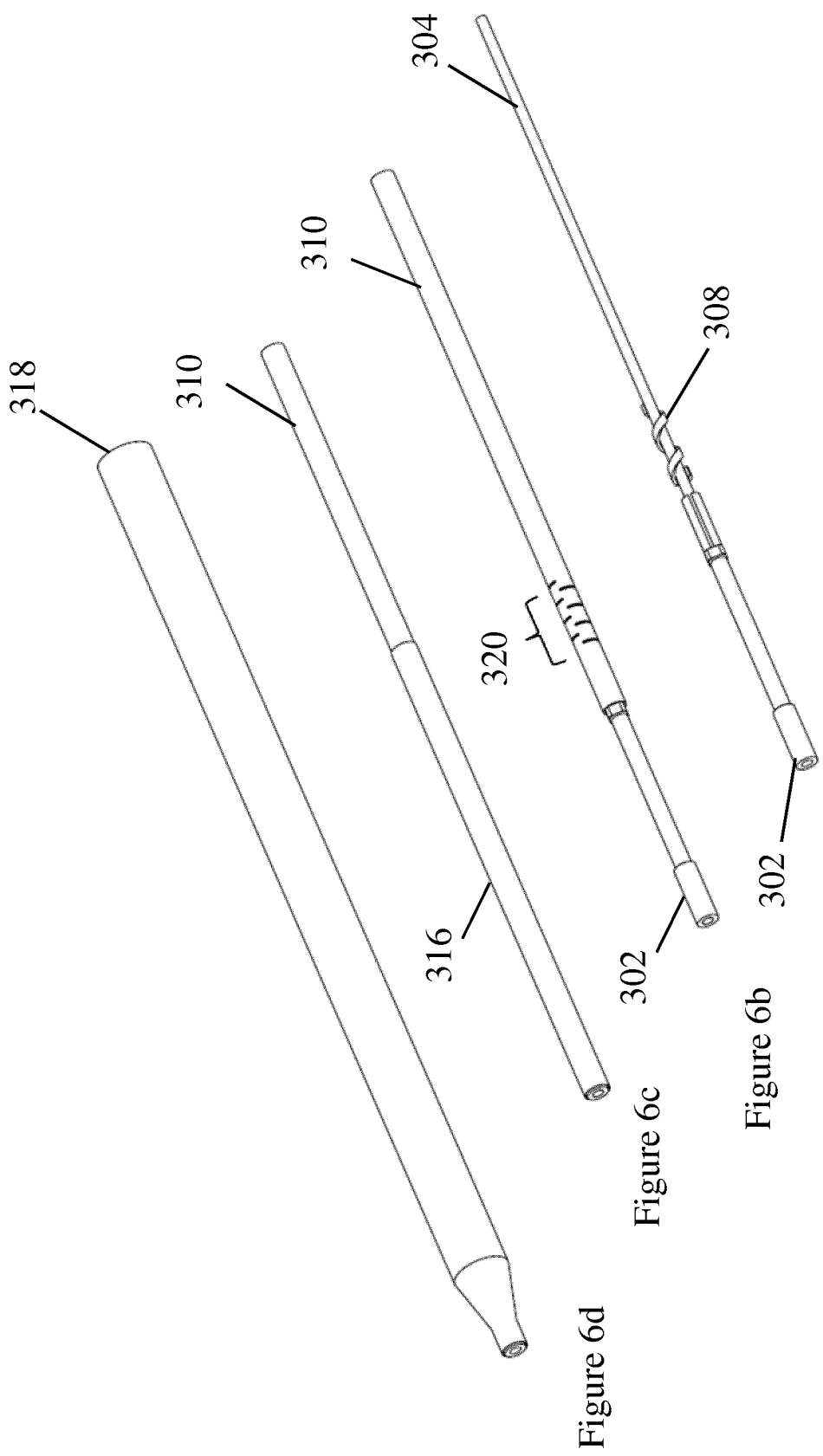
FIGS. 6a to 6d show the ablation probe of FIG. 5 in various states of assembly.

The pattern of holes forming the hinge portion 320 shown in FIGS. 5 and 6 is only one example. In other embodiments, the hole(s) or other weakened portions(s) may have any other suitable shape, size or orientation required to achieve the desired level and direction of flexing. For example, in some embodiments, the hinge portion 320 may be formed by one or more helical slots running along the length of the first surrounding member 310.

The one or more holes extending through the first surrounding member 310 to form the hinge member 320 may be arranged to allow coolant to flow along the coolant flow path. The hinge portion 320 may therefore have the combined function of providing improved flexibility and also allowing the flow of coolant through the ablation probe 300. In such an embodiment, the size and/or shape of the holes may be arranged to provide a balance between mechanical strength and low resistance to the flow of coolant. In the described embodiment, the hinge portion 320 is arranged to fluidly connect the feeding cable cooling portion of the coolant flow path to the ablation probe cooling portion. In other embodiments, the hinge portion may fluidly connect the feeding cable cooling portion to the return portion.

The spiral member described in connection with the embodiment of FIGS. 4 to 6*d* may be replaced by a choke member of any other embodiment described herein.

In some embodiments (not shown in the Figures) the ablation probe 300 may further comprise at least one temperature sensor arranged to provide information on the temperature of the ablation probe at one or more different positions. In some embodiments, the temperature sensor(s) may comprise a thermocouple arranged to measure the temperature of the ablation probe.

In some embodiments, the temperature sensor(s) may be integrated with, or formed by, at least part of the spiral member 308 (or choke member). In such an embodiment, part or all of the length of the spiral member 308 (or other embodiment of the choke member) may be formed from a bimetal portion arranged to form a thermocouple. This may allow the temperature of the choke member to be accurately determined, and may provide feedback to the operator on the ablation zone produced by the applicator 302. By providing a temperature sensor which is integral with, or is formed by, the spiral member 308 (or other choke member) a separate temperature sensor component may not be required. This may help to reduce the overall size of the ablation probe 300 and achieve a small and compact arrangement. In other embodiments, additional or alternative temperature sensors may be provided at other locations within the ablation probe 300. In yet other embodiments, some of the temperature sensors may be any other suitable type of temperature sensor.

FIGS. 7 to 9*c* are provided to demonstrate the performance of an ablation probe according to an embodiment of the present application. The data shown in FIGS. 7 to 9*c* show a comparison of the embodiment shown in FIG. 4 with other ablation probes.

Figure 1:
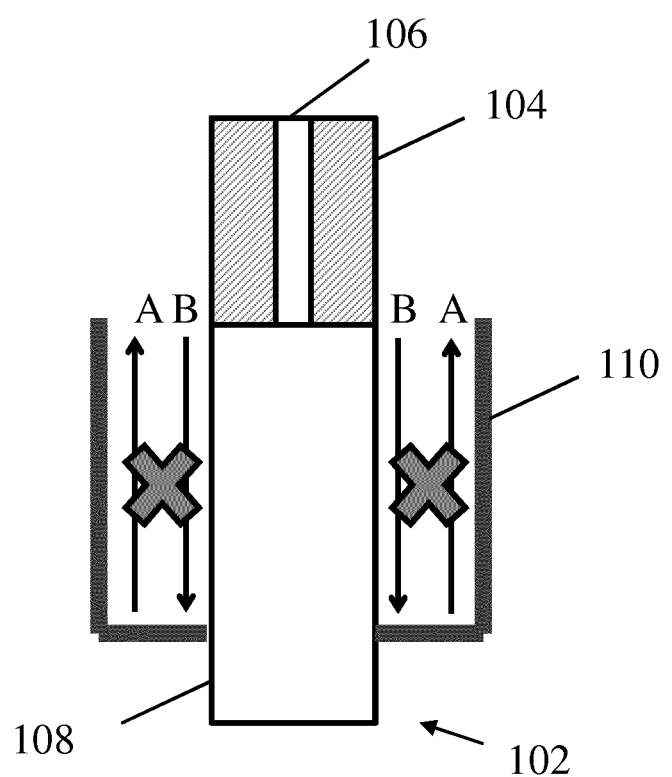
FIG. 1 shows an example of a prior art choke.
Figure 7:
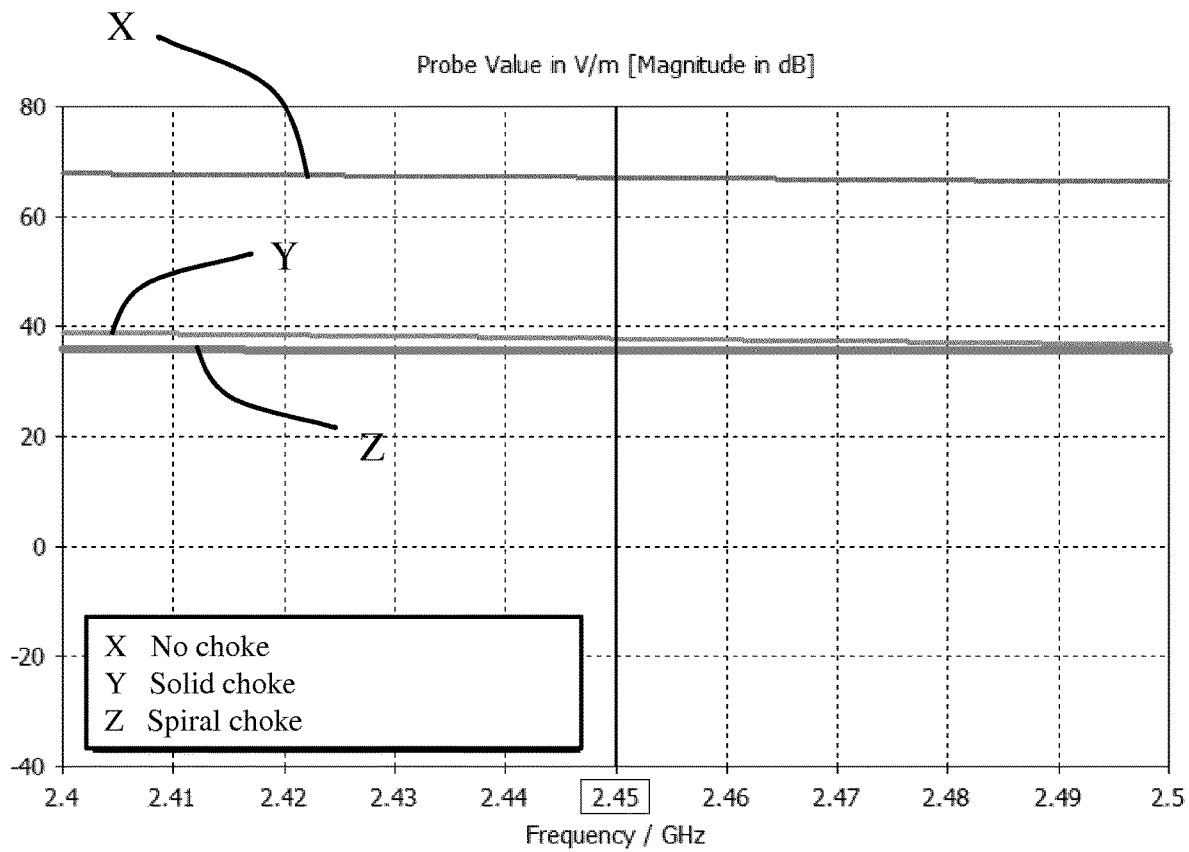
FIG. 7 shows the simulated results of a comparison of the electric field captured by an ideal probe located on the outer conductor of the feeding cable of an ablation probe without a choke, with a prior art solid choke, and with a choke comprising a spiral member according to an embodiment.

FIG. 7 shows a plot of the electric field generated around ablation probes having different choke arrangements. The electric field values in FIG. 7 are the simulated result of calculating the electric field on the outer conductor of the feeding cable at an ideal probe point between the proximal end of the ablation probe and the choke as a function of the frequency of energy supplied to the applicator. The results are shown for ablation probes having different choke arrangements. Line X in FIG. 7 shows the electric field generated by an ablation probe having no choke, line Y shows the electric field generated by an ablation probe having a solid prior art choke (e.g. as shown in FIG. 1) and line Z shows the electric field produced by an ablation probe having a choke comprising a spiral member (e.g. as shown in FIG. 4). The electric field is proportional to a reflected current flowing back along the feeding cable.

As can be seen in FIG. 7, an ablation probe having no choke produces a high electric field indicating the presence of a significant amount of current being reflected back along the feeding cable from the applicator. An ablation produce having a prior art solid choke produces an electric field that is less than where no choke is provided, indicating a reduction in current reflected along the feeding cable. Finally, an ablation probe having a choke comprising a spiral choke member according to an embodiment of the present disclosure can be seen produce a further reduction in electric field compared to the prior art choke. A 47% reduction in back current (at an operating frequency of 2.45 GHz) may be produced by the choke having a spiral member.

Figure 8:
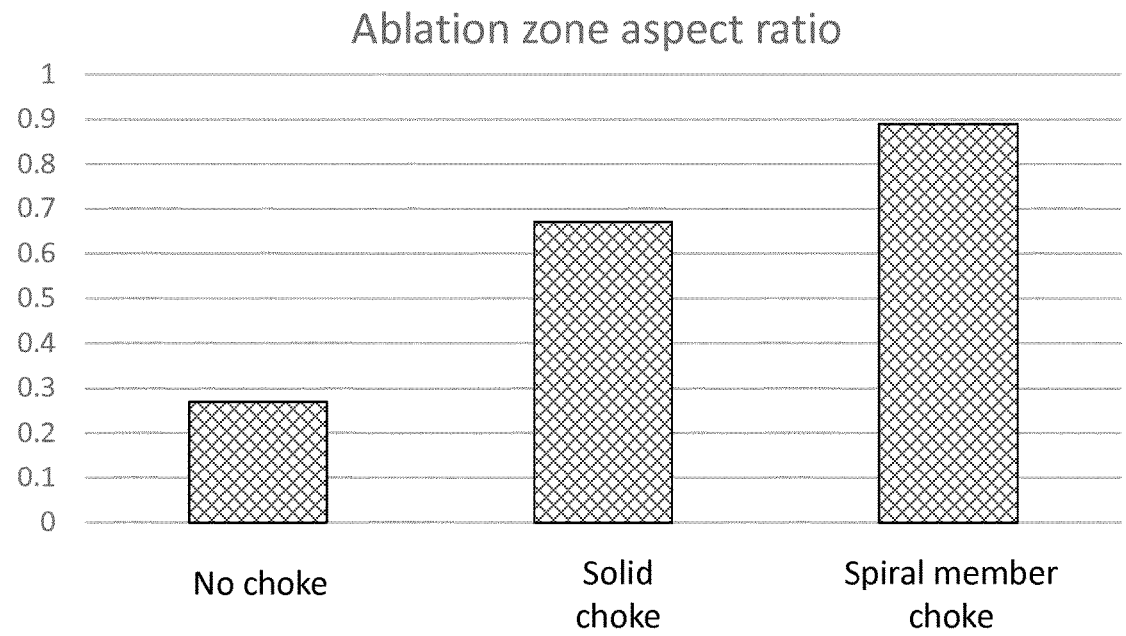
FIG. 8 shows the aspect ratio of the ablation zone produced by an ablation probe according to an embodiment compared to other examples.

FIG. 8 shows a comparison of a simulation of the aspect ratio of ablation zones produced by ablation probes having different choke arrangements. As can be seen in FIG. 8, an ablation probe having no choke produces a tapered ablation zone having an aspect ratio of 0.27. An ablation probe having a prior art solid choke (e.g. as shown in FIG. 1) produces a less tapered ablation zone having an aspect ratio of 0.67. An ablation probe having a choke comprising a spiral member according to an embodiment of the present application may produce an even less tapered ablation zone having an aspect ratio of 0.89. The ablation probe of the present application may therefore produce an ablation zone that is more spherical in shape. This may allow the ablation zone to be more accurately controlled during use and may allow ablation of tissue to be applied more accurately and reliabily.

FIGS. 9a, 9b and 9c show example representations of ablation zones produced by ablation probes having differing levels of cooling with/without chokes. FIG. 9a shows an ablation zone produced by an ablation probe having no choke and inefficient cooling. The aspect ratio of the ablation zone in FIG. 9a is less than 0.5. As can be seen in FIG. 9a, without a choke and efficient cooling the resulting ablation zone is tapered in shape.

FIG. 9b shows an ablation zone produced by an ablation probe having no choke but with efficient cooling of the applicator. In this example, the aspect ratio of the ablation zone is 0.68. The increase in cooling in comparison to FIG. 9a can be seen to produce a less tapered shaped ablation zone.

FIG. 9c shows an example of the ablation zone produced by an ablation probe of the present application (e.g. using a choke comprising a cooled spiral member). The ablation zone produced by the ablation probe of the embodiment shown in FIG. 4 has an aspect ratio of 0.9. The ablation probe of the present application therefore produces an ablation zone that is less tapered and closer to spherical in shape. This may allow the ablation zone to be more accurately controlled during use and may allow ablation of tissue to be applied more accurately and reliably.

Another embodiment of an ablation probe 400 according to an embodiment of this disclosure is shown in FIGS. 10a to 12b. The embodiment shown in these Figures is to be understood as only one example. Features in FIGS. 10a to 12b that are common to the embodiment of FIG. 2 or 4 to 6d are labelled accordingly.

The ablation probe 400 shown in FIGS. 10a to 12b generally comprises an applicator 402, a feeding cable 404, a spiral member 408 (which may be replaced by any other embodiment of the choke member as described above) and a first surrounding member 410. The feeding cable 404 comprises an inner conductor 412 and an outer conductor 414. In this embodiment, the ablation probe 400 also further comprises a deformable member 418 corresponding to that described above. Any of the features described herein in connection with any other embodiment may also be used in the embodiment shown in FIGS. 10a to 12b, and vice versa.

In the embodiment shown in FIGS. 10a to 12b, the applicator 402 comprises an antenna portion 402a of the inner conductor 412 and an overlapping antenna member 402b. The antenna portion 402a of the inner conductor extends from a distal end of the outer conductor 414. The overlapping antenna member 402b is arranged to overlap the antenna portion 402a of the inner conductor 412 along at least part of the length of the antenna portion 402a (e.g. they overlap each other in a direction along the longitudinal axis of the ablation probe labelled Y in FIG. 2). The overlapping antenna member 402b may therefore at least partly surround the antenna portion 402a of the inner conductor 414. The overlapping antenna member 402b is electrically coupled to the inner conductor 412 such that the signal provided by the feeding cable passes along the antenna portion 402a and then along the overlapping antenna member 402b. In order to carry the signal from the inner conductor 412 the overlapping antenna member 402b is therefore formed from any suitable electrically conducting material such as a metal.

The applicator 402 is therefore formed from a combination of a straight monopole antenna, formed by the antenna portion 402a of the inner conductor, and the overlapping antenna member 402b. This may allow a shorter applicator to be provided, while still allowing for the application of electromagnetic energy in the desired frequency range. The overall length of the applicator 402 may, for example, be about 8 mm or less. The combination of the antenna portion 402a and overlapping member 402b thus form a miniaturised monopole antenna.

Reducing the length of the applicator may have a number of advantages. The combination of the overlapping antenna member 402b and choke spiral member 408 (or other embodiment of the choke member) described above may be advantageous in providing a suitably flexible ablation probe that can be delivered to an ablation site along a tortuous route. Furthermore, the shorter length of the applicator may help to facilitate a fully cooled structure to reduce charring and antenna detuning during use. The aspect ratio of the ablation zone may also be improved by reducing the length of the applicator. An applicator that is shorter will naturally provide a more spherical ablation zone because the length of the applicator is more comparable to its width.

The overlapping antenna member 402b may be formed from an elongate component arranged to follow a number of different paths such that it overlaps with and at least partly surrounds the antenna portion 402a of the inner conductor 412. Examples of possible shapes of overlapping antenna member 402b are shown in FIGS. 13a to 16b.

In order to provide the required radiation of energy from the applicator, the overlapping antenna member 402b forms one or more turns around the antenna portion of the inner conductor. The overlapping antenna member 402b may therefore comprise one or more sections extending around and/or along the length of the antenna portion of the feeding cable. Each of the sections may be straight or curved depending on the geometry of the antenna member. The geometry of the overlapping antenna member may have a minimum spacing parameter, the minimum spacing parameter being greater than 0.05% of the wavelength of the radiation emitted by the applicator measured in air. The minimum spacing parameter may correspond to separation of corresponding points in a repeated pattern formed by the overlapping member (e.g. the period or pitch). This may allow the antenna to be miniaturised, without causing significant cancellation of signals resulting from the sections of the overlapping antenna member 402b being too close together. The minimum spacing parameter is labelled m in FIGS. 13a, 14a, 15a, and 16a.

In the example shown in FIGS. 13a and 13b the overlapping antenna member 402b extends along a spiral path around the antenna portion 402a of the inner conductor 412. The spiral path may form a helical path around the inner conductor as shown, and may correspond to the shape of the spiral member 208 of the choke. In this case, the minimum spacing parameter corresponds to the pitch of the spiral being greater 0.05% of the wavelength of the radiation emitted by the applicator measured in air. In the described embodiment, the overlapping antenna member 402b comprises a spiral portion 402d and a cylindrical portion 402e (as illustrated in FIG. 11a). The cylindrical portion 402d may be located at a distal end of the overlapping antenna member 402b. The cylindrical portion 402d may be similar in shape to the locating portion 208a provided in the spiral choke member 208. The cylindrical portion 402d may help to enhance the electromagnetic performance and mechanical durability of the antenna.

In the example shown in FIGS. 14a and 14b, the overlapping antenna member 402b extends along a looped path around the antenna portion 402a of the inner conductor 412. The looped path may correspond to the shape of the choke member 209 shown in FIG. 3b. The overlapping antenna member 402b may therefore similarly comprise one or more curved portions extending part way around the antenna portion 402a of the inner conductor 412, the one or more loop portions being separated by one or more connecting portions extending in a direction along the length of the inner conductor 412. The one or more curved portions may extend in a plane orthogonal to a longitudinal axis of the antenna portion of the inner conductor, and be spaced apart along that longitudinal axis by the connecting portions. In this case, the minimum spacing parameter corresponds to a separation of the loop portions along the length of the antenna portion of the inner conductor being greater than 0.05% of the wavelength of the radiation emitted by the applicator measured in air.

In the example shown in FIGS. 15a and 15b, the overlapping antenna member 402b extends along a zig-zagged path around the antenna portion 402a of the inner conductor 412. In this case, the minimum spacing parameter corresponds to the period of the zig-zag pattern being greater than 0.05% of the wavelength of the radiation emitted by the applicator measured in air.

In the example shown in FIGS. 16a and 16b, the overlapping antenna member 402b extends along a meandering path around the antenna portion 402a of the inner conductor 412. In this case, the overlapping antenna member comprises a plurality of overlapping longitudinal portions extending in a direction along the length of the antenna portion of the inner conductor, the longitudinal portions being connected by one or more connecting curved portions extending in a direction around the antenna portion 402b. In this case, the minimum spacing parameter corresponds to the period of the meandering pattern being greater than 0.05% of the wavelength of the radiation emitted by the applicator measured in air.

In addition to the antenna portion 402a of the inner conductor 412 and the overlapping antenna member 402b, the applicator may further comprise a dielectric insulator 402c. The dielectric insulator may comprise a dielectric material such as a ceramic material as described above, and may have a pointed tip to allow insertion into tissue as shown in FIGS. 10a and 10b. At least part of the dielectric insulator 402c may be disposed between the antenna portion 402b of the inner conductor 412 and the overlapping antenna member 402b. The overlapping antenna member 402b may, for example, be wrapped around an outer surface of the dielectric resonator 402c. The dielectric resonator 402c may comprise an aperture arranged to receive the distal end of the inner conductor 414, and may extend between the first surrounding member 410 and the outer conductor 414 as described above. A portion of the dielectric insulator 402c may extend distally past the end of the antenna portion 402a of the inner conductor and the overlapping antenna member 402b.

The antenna portion 402a of the inner conductor 412 may extend from the distal end of the outer conductor 414 a distance of between 0.3% and 10% of the wavelength of the microwave radiation emitted by the applicator measured in air. This may provide the desired frequency of emitted radiation, while still providing a small and compact device.

The overlapping antenna member 402b may extend along the length of the antenna portion 402b of the inner conductor 412 a distance of between 0.3% and 20% of the wavelength of the microwave radiation emitted by the applicator measured in air. This may again provide the desired emission frequency and compact design.

The overlapping antenna member 402b may be cooled by coolant flowing in the coolant flow path flowing through the ablation probe 400. For example, the overlapping antenna member may be cooled by coolant delivered via the channel formed between the surrounding member 410 and the outer conductor 414 of the feeding cable 404.

The dielectric insulator 402c may comprise a recessed portion 422, shown more clearly in the close up view of FIG. 11a and 11b. The recessed portion 422 may be formed on an outside surface of the dielectric resonator 402c and is arranged to receive the overlapping antenna member 402b. The recessed portion 422 may be fluidly coupled to the coolant flow path so that a flow of coolant may flow around the overlapping antenna member 402a to facilitate its cooling.

The overlapping antenna member 402b may be formed from a conducting material such as metal. In order to electrically connect the overlapping antenna member 402b and the antenna portion 402a of the inner conductor an electrical connection may be formed through the body of the dielectric resonator 402c. The electrical connection may be formed using a conducting connection pin 424, as shown in FIG. 11b, or metalised hole formed in the dielectric insulator 402c, or both. In other embodiments, the electrical connection may be made using any other suitable method.

In some embodiments, the overlapping antenna member 402b may be formed from a separate component wrapped around the surface of the dielectric insulator 402c. In other embodiments, the overlapping antenna member 402b may be formed by plating a conducting material, e.g. metal, onto the surface of the dielectric insulator 402c.

In some embodiments, the overlapping antenna member 402b may be formed from a portion of the inner conductor 412. The overlapping antenna member 402b may, for example, be formed by wrapping part of the inner conductor 412 of the feeding cable around the dielectric insulator 402c as it exits from a hole in the dielectric insulator 424.

The applicator 402 may further comprise a sleeve member 426. The sleeve member 426 may be arranged to at least partly surround the overlapping antenna member 402b to restrict the transfer of heat from the overlapping antenna member 402b to other parts of the ablation probe. The sleeve member 426 may, for example, reduce the transfer of heat to the deformable member 418, or other surrounding parts of the ablation probe which may be present. One or more through holes 428 may be provided in the sleeve member 426 to allow the flow of coolant from the deformable member 418 into the recessed portion 422 of the dielectric resonator 402c to allow coolant to flow around the overlapping antenna member 402b. Coolant may flow into the sleeve member via one or more holes 410a extending through the first surrounding member 410. The sleeve member may be formed from any suitable heat resistant material such as polyamide. The sleeve member 426 may therefore correspond to the second surrounding member 316 described above.

In the embodiment described in FIGS. 10a and 10b the overlapping member is provided in combination with the spiral member (or other shaped choke member) and the deformable member forming the coolant flow path. In other embodiments, the overlapping member may be used separately to form part of the applicator of an ablation probe.

The invention claimed is:

1. A microwave ablation probe, comprising:
   an applicator arranged to apply microwave radiation to heat surrounding tissue;

a feeding cable arranged to supply electromagnetic energy to the applicator;
a coolant flow path via which coolant is able to flow; and
a choke arranged to reduce power reflected from the applicator along the feeding cable, wherein the choke comprises:
a choke member cooled by coolant flowing in the coolant flow path,
wherein the choke member is a spiral member extending between two points spaced apart in a direction having at least a component parallel to a longitudinal axis of the feeding cable, the choke member comprising one or more turns extending around the longitudinal axis of the feeding cable.

2. The ablation probe according to claim 1, wherein the spiral member forms a helix extending along the length of the feeding cable.

3. The ablation probe according to claim 1, wherein the choke member comprises one or more curved portions extending around the longitudinal axis, the one or more curved portions being linked by one or more connecting portions extending in a direction having at least a component parallel to the longitudinal axis, and optionally wherein the one or more curved portions extend in a plane orthogonal to a longitudinal axis of the feeding cable.

4. The ablation probe according to claim 3, wherein the pitch of the spiral member or the axial separation of the one or more curved portions is proportional to approximately one quarter of the wavelength of the electromagnetic energy corresponding to the operating frequency of the ablation probe, and preferably wherein the distance corresponds to approximately a multiple of an odd number of one quarter of the wavelength of the electromagnetic energy in a medium surrounding the feeding cable.

5. The ablation probe according to claim 1, wherein: a) the choke member is disposed at least partly within the coolant flow path; and/or b) the coolant flow path is arranged to provide a uniform flow of coolant around at least part of the length of the feeding cable and/or around the choke member.

6. The ablation probe according to claim 1, further comprising a first surrounding member arranged to at least partly surround the feeding cable, wherein the choke member is disposed within the first surrounding member, and preferably wherein the first surrounding member comprises a tube arranged to surround the feeding cable.

7. The ablation probe according to claim 6, wherein the coolant flow path comprises a feeding cable cooling portion comprising a channel formed between the feeding cable and the first surrounding member, and wherein the choke member is arranged within the channel.

8. The ablation probe according to claim 7, wherein the choke member is arranged to space apart an outer surface of the feeding cable and an inner surface of the first surrounding member to form the channel, and preferably wherein the choke member is arranged to concentrically align the feeding cable and the first surrounding member relative to each other.

9. The ablation probe according to claim 6, wherein the choke member is arranged to electrically connect the first surrounding member to the feeding cable such that part of the first surrounding member forms part of the choke.

10. The ablation probe according to claim 9, wherein the feeding cable comprises an inner conductor and an outer conductor, and wherein the choke member forms an electrical connection between the outer conductor of the feeding cable and the first surrounding member, and preferably wherein the electrical connection is formed at a distance spaced along the length of the feeding cable from a distal end of the outer conductor, and further preferably wherein the distance is proportional to approximately a multiple of an odd number of one quarter of the wavelength of the electromagnetic energy corresponding to the operating frequency of the ablation probe, and even further preferably wherein the distance corresponds to approximately a multiple of an odd number of one quarter of the wavelength of the electromagnetic energy in a medium surrounding the feeding cable.

11. The ablation probe according to claim 9, wherein the choke comprises a choke region surrounding part of the feeding cable, the choke region being defined by the choke member and at least part of the first surrounding member, and optionally wherein the choke region is at least partly filled with:
a) coolant flowing in the coolant flow path; and/or
b) a portion of the applicator arranged to extend between the feeding cable and the first surrounding member.

12. The ablation probe according to claim 6, wherein the first surrounding member comprises a hinge portion, the hinge portion arranged to increase the flexibility of the first surrounding member, and wherein optionally the hinge portion is arranged:
a) between a proximal end of the applicator and a distal end of the choke member; and/or
b) so as to overlap with at least part of the choke member along the length of the feeding cable.

13. The ablation probe according to claim 12, wherein the hinge portion comprises one or more weakened portions formed in the first surrounding member, and optionally wherein the weakened portions are arranged to encourage flexing of the ablation probe.

14. The ablation probe according to claim 12, wherein the hinge portion is formed by one or more holes extending through the first surrounding member, and preferably wherein the one or more holes are arranged to allow coolant to flow.

15. The ablation probe according to claim 14, wherein the coolant flow path comprises an applicator cooling portion arranged to deliver a flow of coolant to at least part of the applicator, and optionally wherein any one or more of:
a) the one or more holes are arranged to fluidly couple the applicator cooling portion to a cable cooling portion of the coolant flow path;
b) wherein the ablation probe comprises a second surrounding member arranged to surround at least part of the applicator and/or the first surrounding member, wherein the applicator cooling portion comprises a channel formed between the second surrounding member and one or both of the applicator and first surrounding member; and
c) the applicator cooling portion comprises one or more channels in the surface or body of the applicator.

16. The ablation probe according to claim 1, further comprising at least one temperature sensor, wherein any one of:
a) the at least one temperature sensor comprises a thermocouple;
b) the at least one temperature sensor is integrated with, or is formed by, at least part of the choke member.

17. The ablation probe according to claim 1, the feeding cable comprising:
i) an inner conductor, and;
ii) an outer conductor, wherein the applicator comprises:
an antenna portion of the inner conductor, the antenna portion extending from a distal end of the outer conductor; and
an overlapping antenna member electrically coupled to the inner conductor, the overlapping antenna member at least partly overlapping the antenna portion of the inner conductor along the length of the antenna portion of the inner conductor.

18. The ablation probe according to claim 17, wherein the overlapping member comprises one or more turns around the length of the antenna portion of the feeding cable, and optionally wherein the geometry of the overlapping member has a minimum spacing parameter, the minimum spacing parameter being greater than 0.05% of the wavelength of the radiation emitted by the applicator measured in air.

19. The ablation probe according to claim 17, wherein the applicator further comprises a dielectric insulator, at least part of the dielectric insulator being disposed between the antenna portion of the inner conductor and the overlapping antenna member, and optionally wherein the dielectric insulator comprises an outer surface having a recessed portion, the recessed portion arranged to receive the overlapping antenna member.

20. The ablation probe according to claim 17, wherein any one or more of:
a) the antenna portion of the inner conductor extends from the distal end of the outer conductor a distance of between 0.3% and 10% of the wavelength of the microwave radiation emitted by the applicator measured in air; and/or
b) the overlapping antenna member extends along the length of the antenna portion of the inner conductor a distance of between 0.3% and 20% of the wavelength of the microwave radiation emitted by the applicator measured in air; and/or
c) the overlapping antenna member is cooled by coolant flowing in the coolant flow path; and/or
d) the applicator further comprises a sleeve member, the sleeve member arranged to at least partly surround the overlapping antenna member to restrict the transfer of heat from the overlapping antenna member.

* * * * *